US012125595B2

United States Patent
Maddess et al.

(10) Patent No.: US 12,125,595 B2
(45) Date of Patent: Oct. 22, 2024

(54) RESPONSE ESTIMATION TO EFFICIENTLY CAPTURE DYNAMIC RESPONSE GAIN CHANGES IN MULTIFOCAL RESPONSES

(71) Applicant: Konan Medical USA Inc., Irvine, CA (US)

(72) Inventors: Teddy Lee Maddess, Lyneham (AU); Joshua Paul Van Kleef, Chapman (AU); Corinne Frances Carle, Bywong (AU)

(73) Assignee: Konan Medical USA, Inc., Irvine, CA (US)

( * ) Notice: Subject to any disclaimer, the term of this patent is extended or adjusted under 35 U.S.C. 154(b) by 0 days.

(21) Appl. No.: 18/588,429

(22) Filed: Feb. 27, 2024

(65) Prior Publication Data

US 2024/0212858 A1     Jun. 27, 2024

Related U.S. Application Data

(63) Continuation of application No. PCT/AU2023/050169, filed on Mar. 10, 2023.

(51) Int. Cl.
*A61B 3/11*     (2006.01)
*A61B 5/16*     (2006.01)
(Continued)

(52) U.S. Cl.
CPC ............. *G16H 50/30* (2018.01); *G16H 20/40* (2018.01); *G16H 40/60* (2018.01); *A61B 3/112* (2013.01); *A61B 5/163* (2017.08)

(58) Field of Classification Search
CPC ..... A61B 3/024; A61B 3/0025; A61B 3/0041; A61B 3/112; A61B 3/113; A61B 5/4005;
(Continued)

(56) References Cited

U.S. PATENT DOCUMENTS

| 5,539,482 A | 6/1996 | James et al. |
| 6,086,206 A | 7/2000 | Sutter |

(Continued)

FOREIGN PATENT DOCUMENTS

| WO | 2009059380 A1 | 5/2009 |
| WO | 2014078909 A1 | 5/2014 |

OTHER PUBLICATIONS

Lee et al., "Measurement of the Weiner Kernels of a Non-linear System by Cross-correlation", International Journal of Control, 1965, vol. 2, pp. 237-254.

(Continued)

*Primary Examiner* — Brandi N Thomas
(74) *Attorney, Agent, or Firm* — LaBatt, LLC

(57) ABSTRACT

Estimating the responses of multiple parts of the visual fields of one or both eyes from records of the responses of one or both pupils to concurrently presented multifocal stimuli to the multiple parts of those visual fields. Collections of multifocal stimuli are controlled by separate pseudo-random sequences, one sequence for each stimulated visual field region. Both temporal impulse responses for each component part of the field and gain-kernels characterizing dynamic changes in the pupil responses driven by short-term fluctuations in overall stimulus density are estimated. Many fewer kernels can be estimated by grouping the stimuli into symbolic stimulus groups and only estimating a gain-kernel for each group. Particular symbolic stimulus groups are shown to be highly efficient. The ability to estimate more reliable responses with relatively few extra gain-kernel coefficients means less data is required to be collected.

30 Claims, 11 Drawing Sheets

(51) Int. Cl.
  *G16H 20/40* (2018.01)
  *G16H 40/60* (2018.01)
  *G16H 50/30* (2018.01)

(58) Field of Classification Search
  CPC ..... A61B 3/032; A61B 3/1173; A61B 5/1104; A61B 5/378; A61B 3/005; A61B 3/14; A61B 5/0077; A61B 5/1114; A61B 5/1128; A61B 5/163; A61B 5/4047; A61B 5/7425
  See application file for complete search history.

(56) References Cited

U.S. PATENT DOCUMENTS

| | | | |
|---|---|---|---|
| 7,006,863 | B2 | 2/2006 | Maddess et al. |
| 8,583,223 | B2 | 11/2013 | Maddess et al. |
| 9,848,771 | B2 | 12/2017 | Maddess et al. |
| 2008/0108908 | A1 | 5/2008 | Maddess et al. |
| 2011/0292342 | A1 | 12/2011 | Maddess et al. |
| 2019/0307399 | A1* | 10/2019 | Gutierrez ............... G02C 7/083 |

OTHER PUBLICATIONS

James et al., "Effect of temporal sparseness and dichoptic presentation on multifocal visual evoked potentials", Visual Neuroscience, 2005, vol. 22, pp. 45-54.

Goh, "Cortical generators of human multifocal visual evoked potentials and fields", 2008 PhD thesis, The Australian National University, DOI: 10.25911/5d51548ee0131, 401 pages.

Inverso, et al., "From Evoked Potentials to Cortical Currents: Resolving V1 and V2 Components Using Retinotopy Constrained Source Estimation Without fMRI", Human Brain Mapping, vol. 37, 2016, pp. 1696-1709.

Carle, et al., "High-Resolution Multifocal pubillographic Objective Perimetry in Glaucoma", Investigative Ophthalmology & Visual Science, Jan. 2011, vol. 52, No. 1, pp. 604-610.

Carle, "Localization of Neuronal Gain Control in the Pupillary Response", Frontiers in Neurology, vol. 10, Mar. 12, 2019, 9 pgs.

Maddess, "Contrast response of temporally sparse dischoptic multifocal visual evoked potentials", Visual Neuroscience, Mar. 2005, vol. 22, pp. 153-162.

International Search Report and Written Opinion for International Application No. PCT/AU2023/050169, May 31, 2023, 12 pages.

* cited by examiner

RESPONSE ESTIMATION TO EFFICIENTLY CAPTURE DYNAMIC RESPONSE GAIN CHANGES IN MULTIFOCAL RESPONSES

REFERENCE TO RELATED CASES

The present invention is a continuation of International Application No. PCT/AU2023/050169, filed on 10 Mar. 2023, which claims priority to and the benefit of Australian Provisional Application No. 2022900601, filed on 11 Mar. 2022, each of which is hereby incorporated by reference.

TECHNICAL FIELD

The present invention relates generally to methods and systems for concurrently assessing functional aspects of many parts of the visual fields of persons or animals. More specifically the invention relates to determining how the history of stimuli presented over about 1 second influences the response to subsequent stimuli, most particularly when the balance of the concurrently presented stimuli switches from one eye to the other.

BACKGROUND

Any discussion of the background throughout the specification should in no way be considered as an admission that such background is prior art, nor that such background is widely known or forms part of the common general knowledge in the field.

Multifocal stimulation of the nervous system refers to presenting over time different sequences of stimuli to different parts of the sensory apparatus. For example, one might have four buzzers attached to different parts of the skin of the forearm. Four different temporal sequences might then determine when each buzzer stimulates the skin at its location. This is a multifocal presentation of concurrent tactical stimuli across the sensory field of the forearm. In the visual case, the visual fields of one or both eyes are divided into multiple regions, and then a visual property of each region; like the color, contrast, brightness, or texture, is independently modulated over time according to a set of temporal sequences, one for each region of the visual field or visual fields. The stimulus sequences are records of the stimulus history for each stimulated region. In either example, some recordal means is used to record the pooled response of the nervous system to the multifocal stimuli.

A classical recordal method is to record an evoked electrical response of the nervous system to the stimuli. In the tactile or visual examples just given one could record electrical responses of the brain by placing electrodes on the scalp, to capture the response of the brain to the stimuli. These records contain a version of the sum of all the responses to the multiple, concurrently presented, stimuli. If just one region was stimulated at a time the brain activity would reflect responses of just one region and one could estimate the response by averaging with respect to the onset of each stimulus in the sequence. When several stimuli are presented concurrently one has the problem of how to estimate separate average responses to the stimuli delivered to each sensory region. This can be achieved when the temporal sequences driving stimulus presentations at each region are statistically independent, that is to say if they are substantially uncorrelated in time. Then methods like cross-correlation between the evoked response and the stimulus histories, or some form of multiple regression between the evoked response and the stimulus history, i.e. a record of the stimulus sequences, can yield the average response at every stimulated region.

Up to the present time patents related to multifocal methods have been concerned with particular categories of stimulus sequences, or the spatio-temporal coordination of patterns of sequences. An early example included near-orthogonal pseudo-random sequences that were designed to make response estimation by cross-correlation efficient: EE Sutter, U.S. Pat. No. 6,086,206. Those methods did not suggest that any particular temporal rate or density of stimulation was optimal. Later, the inventor of the disclosed invention obtained patents towards methods to generate stimuli that have particular temporal or spatial densities that were unexpectedly found to produce responses that were many times larger and more reliable: T Maddess and A C James, U.S. Pat. Nos. 7,006,863 and 8,583,223. Those patents showed that if stimuli are kept apart in time or space that the average gain, i.e. the average responsiveness of the system, is higher. Thus, for example U.S. Pat. No. 7,006,863 focused on the idea that: "appropriate design of stimulus sequences might permit neural systems . . . to produce larger and or more reliable responses". U.S. Pat. No. 8,583,223 focused on an effect known as "lateral masking" whereby spatially adjacent stimuli can suppress responses to each other and accordingly to minimize the deleterious effects of lateral masking that patent said "response sizes and reliability can be improved by insuring that concurrently presented stimuli are separated in space, thus such stimuli are said to be spatially sparse".

Subsequently investigations moved from evoked electrical responses to using responses of pupils by recording time-varying changes in pupil diameter. Unlike evoked electrical responses, imaging and video monitoring of the pupils provides a non-contact form of multifocal assessment. Due to the connectivity of the nervous system driving the pupils, each pupil reports on a version of the sum of the activity of the two retinas. Thus, response estimation from a single pupil record can produce average responses to stimuli presented concurrently to multiple stimulus regions of the two eyes. Therefore, recording both pupils yields two sets of responses for each eye. The move to pupil recording resulted in two pupil-specific patents.

The first of these patents involved the so-called luminance balancing method: T Maddess and A C James; U.S. Pat. No. 8,583,223. This involved keeping the average gain, i.e. responsiveness, across different test regions about equally high. Average gain refers to the mean response per unit stimulus strength obtained from across a set of concurrently stimulated visual field regions over the duration of the test. The method was based on the discovery that some hyper-responsive regions from the superior-temporal visual field naturally respond more than other areas on average when stimuli of the same intensity are presented to each region. These hyper-responsive regions set the average response gain of the pupillary system lower, reducing the relative responsiveness of other areas. By reducing the stimulus strength delivered to naturally hyper-responsive regions the average gain across the test period is kept higher, thus increasing the responses of naturally less sensitive visual field regions. By inverting a static nonlinear stimulus-response function the stimuli strengths were balanced across the visual field. Thus, U.S. Pat. No. 8,583,223 indicated that by: "decreasing the luminance of stimuli that are presented to more responsive regions in the visual field reduces the contributions to the overall pooled driving signal to the (pupil), thereby increasing the absolute response size of normally less responsive regions.".

A second pupil-specific patent involved so-called clustered-volleys, T Maddess, CF Carle and A C James; U.S. Pat. No. 9,848,771. This involved the discovery that even for luminance balanced stimuli there was a further advantage to presenting stimuli in spatially adjacent clusters within subsets of regions of the visual field. In a non-limiting demonstration, these were chosen to be clusters within left vs right, or superior vs. inferior half of the field. This was surprisingly opposite to that predicted by publication, U.S. Pat. No. 8,583,223. This method kept the number of stimuli presented on any one time step of the test relatively constant maintaining reasonably balanced average gain. This did not occur in previously patented stimulus methods where the average number of stimuli per time step was more free to vary.

In the pupillary system a set of inputs arising in the two retinas proceeds to the left and right pretectal olivary nucleus (PON), and then from each to both the left and right Edinger-Westphal Nucleus (EWN), each of which innervates its respective left or right iris to produce the pupillary light response. Each PON also gets visual input from its left or right visual cortex. Each EWN in turn receives input from both PONs, this is how each pupil responds to the sum of activity on both retinas as mentioned earlier. In an elaborate set of experiments presented in U.S. Pat. No. 9,848,771 it was concluded that there was "a gain control mechanism at the EWN or afterwards on the path to the pupil", and that "This gain control system tends to diminish responses of the pupil less when multiple visual stimuli are presented in volleys of spatially adjacent clusters of stimuli, compared to earlier methods such as temporally or spatially sparse stimuli". The patent went further to say the finding presented: "suggested that the EWN gain control involved a feed-back mechanism that was too slow to dampen down the stimuli when the stimuli were delivered in volleys". Thus, U.S. Pat. No. 9,848,771 had two core ideas: that the gain control mechanisms regulating average gain across the field occurred at the level of the EWN, by which time combination of the inputs for the two eyes and visual cortices was completed, and that the mechanism was too slow to be affected by sequence of juxtaposed volleys, which in U.S. Pat. No. 9,848,771 occurred at a rate of one every quarter second.

It was discovered that interactions between particular sequential volleys can have a marked effect on short-term gain. Whereas, previous publications, such as U.S. Pat. No. 9,848,771, indicated that the results of all volleys from the whole of both retinas were pooled in the EWN and that result regulated gain, leaving no place for special contributions by each eye.

All the above-mentioned methods specified different types of multifocal stimulus sequences, or different spatio-temporal coordination of sequences, whereby every test subject received the same, allegedly optimal stimuli. Similarly, the same response estimation methods were used for every test subject and every patented stimulus sequence variant. In concentrating on the average gain, and fixed response estimation, these methods did not indicate that there would be any advantage in assuming that the dynamic gain characteristics of individuals would differ, or that there would be any advantage to tailoring the response estimation method to individual persons or pupils. Indeed, those patents presented evidence that no such dynamic effects occur and, as mentioned, U.S. Pat. No. 9,848,771 went so far as to say the system regulating responsiveness in the EWN was too slow to react to random volleys of stimuli presented at intervals of 0.25 seconds.

All response estimation methods employed in multifocal test methods used to date assume that if there are nonlinearities in the systems being examined, that these are static. That is, those nonlinearities remain unchanged over the course of the test. As mentioned the classical response estimation method involves cross-correlation between the stimulus histories, i.e. the set of test sequences that controlled presentations at each region, and a response of the nervous system containing a version of the sum of all the responses, a so-called pooled response. That method was first presented in 1965: in the article by Y. W. Lee and M Schetzen entitled "Measurement of Weiner kernels of a non-linear system by cross-correlation" that appeared in Volume 2, pages 237-254 of the International Journal of Control. That method is still commonly used. The Weiner kernels mentioned in the title of that paper are also called linear and nonlinear weighting functions. The nonlinear kernels capture the effects of additive nonlinear interactions between stimuli. The linear weighting functions are also known as the temporal impulse responses to repeated brief, impulsive, stimuli. Herein are described methods to estimate responses in a system that has dynamic divisive gain control where rapid changes in gain also depending upon the stimulus history, and those dynamics may differ from person to person, and even pupil to pupil. These nonlinearities are not captured using standard functional expansions like Wiener Kernels.

A more flexible, response estimation method based upon multiple linear regression was subsequently presented by A C James, R Ruseckaite, and T Maddess in their 2005 paper entitled, "Effect of temporal sparseness and dichoptic presentation on multifocal visual evoked potentials", published in Visual Neuroscience, volume 22, page 45-54. While more flexible those methods were only suitable for systems with unchanging Wiener nonlinearities. Unlike cross-correlation, regressive response estimation allows features to be added to the response estimation model to account for aspects of the recording or the response in it. For example, when recording evoked electrical responses, it is not unusual for the electrodes to pick up signals from the alternating current mains power supply (hum). Accordingly, one can add terms to the regressive model to partition the variance in the record into separate components for the physiological response and the mains frequency, thus allowing the neural response to be estimated concurrently with hum from the mains. Biological responses often contain a degree of auto-correlation. Cross-correlation based response estimation for multifocal stimuli cannot account for autocorrelation. The result is that the variance due to autocorrelation is mis-assigned in the estimates, appearing as noise. Concurrently estimating the responses to the multifocal stimuli and an autoregressive model as a form of nuisance term is possible and can improve the fitted estimates.

As demonstrated by James et al. 2005 (above) another advantage of the regressive framework is that standard errors (SE) in each of the estimated coefficients can be determined. Thus, if one had 88 stimulus sequences controlling the presentation of brief stimuli at 44 locations in the visual field of each eye, then the response estimation would extract the average size of the response to the presentations at the 88 locations and also 88 SE, one for each response. By contrast, the classical cross-correlation method provides no estimates of error. In principle the regressive frame can be extended to iterative forms of response estimation that can fit nonlinear coefficients.

Mathematically, estimating more coefficients from the same amount of data means that there are fewer data points in the pupil records per estimated coefficient, and therefore the standard error in each estimated coefficient will be larger, that is the estimates will be poorer. That process is like estimating the mean of a data set, i.e. a single coefficient, and its standard error (SE). By definition, the SE is the standard deviation divided by the square root of the number of averaged data points. Thus, the smaller the number of points averaged, the larger the SE. Thus, as in any statistical estimation process, it is not desirable to try to estimate too many things relative to the number of available data points in the pupil records. In principle the multifocal test can be made longer in order to collect more data, but this may make the test longer than is tolerable or desirable.

In the more common tests 44 regions of the visual field of each eye are examined, and both eyes are tested concurrently. The average response amplitude was estimated at each region and the time-to-peak of the response to stimulus presentations at each region. This means, at a minimum, 2 coefficients for 88 regions/pupil record or 176 coefficients were estimated. If even 2 more coefficients were added per region to explain changes in system nonlinearities at that region, then the total would be 2×176=352. Even if this were possible and standard errors would grow by about square root of 2, i.e. over 40%. Thus, any strategy for estimating dynamic nonlinearities should have a strategy to minimize the number of extra coefficients that are to be estimated and still achieve enhanced performance on the basis of being a better model by measures such as the variance accounted for, often referred to as the model $R^2$ or goodness of fit statistic.

As mentioned above, the regressive framework can be extended to iterative forms of response estimation that can fit nonlinear coefficients. A family of such iterative response estimation methods were instituted. The intent of these was to determine if response estimation from pupillary responses to multifocal stimuli could be improved by: 1) including the possibility of rapid fluctuations in responsiveness, i.e. dynamic gain; and 2) whether any such fluctuations could be attributed to recent changes in the stimulus history and estimating coefficients for those changes, in the form of so-called gain-kernels; and 3) whether only small subsets of the possible multitude of gain-kernel coefficients could be efficiently estimated, thus reducing the requirement for vastly more data. Note that the normal temporal impulse responses for each stimulus region would be estimated in the same process such that estimation of the gain-kernels improves the estimates of the regional temporal impulse responses. Another question is whether it was possible or desirable to estimate individual gain-kernels for every test subject, or every pupil, or to fix the values of the gain-kernels for each person that might depend upon factors like their sex and age.

Using those new methods, a series of discoveries that improve the accuracy of the regional temporal impulse response estimates were made. These discoveries demonstrated for the first time that rapid stimulus-history dependent changes in responsiveness should be taken into account for the purposes of response estimation, and that these may be summarized in a surprisingly small set of coefficients, provided rapid changes associated with stimuli switching between eyes are included.

The overall objective of these methods is to efficiently assess the extent and function of the visual fields of persons or animals, in other words to produce data about their visual fields. An example animal might be a race horse. Horses are subject to animal husbandry and so particular horses might have more or less suitable visual field extent for the purposes of being a successful race horse. If the subject were a human visual field data could be used in conjunction with other data to determine the suitability of a person for a given profession, or to determine if they should be allowed to operate particular vehicles. The other data might be metabolic or physical data from the person. The visual field data could also be used to monitor the status of a person. For example, a doctor may have diagnosed a person as being diabetic using blood sugar testing. It might be useful for the doctor to monitor the visual field data of the patient over time for any changes, due to diabetes or things that are more prevalent with diabetes like uncomplicated cataract. Finally, in conjunction with other data a health professional might diagnose a person has having particular eye or brain disease using the conjunction of visual field data and other data, which together could in the opinion of the doctor, or other health professional, be diagnostic. In the clinical setting monitoring the stability of treatment outcomes is likely to be a more common use than assisting with diagnosis, given that a given person might be monitored many times over their lifetime once they had been diagnosed on a single day.

SUMMARY

Embodiments of the current invention reduce a rich set of multifocal stimulus fluctuations into a much smaller set of symbolic stimulus groups, and then a response measurement system fits separate gain-kernels, which summarize dynamic changes in pupil response gain, for each of these groups in parallel along with estimating (i.e. measuring) temporal impulse responses for each multifocal stimulus region. That is, the term "gain-kernel" is to be taken as measuring a dynamic change in pupil response gain. Sets of symbolic stimulus groups with particular properties are shown to be more useful for assessing the visual fields. Said gain-kernels describe how the recent few time steps of the stimulus history affect the responsiveness of the pupillary system to the current stimuli selected from particular symbolic stimulus groups. In characterizing aspects of the pupillary nervous system these stimulus group-dependent gain-kernels are an improvement in response estimation (i.e. measurement) methods for multifocal visual field testing employing recording of the pupils. To illustrate these steps, the non-limiting example of a collection of clustered-volley stimuli is broken down into symbolic stimulus groups, and, through their incorporation in response estimation (i.e. measurement), it is shown that surprising improvements on the original clustered-volley method can be had for the addition of surprisingly few additional coefficients. Stimulus methods other than the clustered-volleys method could have been selected.

BRIEF DESCRIPTION OF THE DRAWINGS

Arrangements of the methods, apparatus and systems are described, by way of an example only, with reference to the accompanying drawings, in which:

FIG. 1D) are active and so become bright and are displayed to the left eye. The bright presented stimuli are shown here as being grey. In this particular example all the stimuli have a duration of 33 ms. The remaining six regions remain inactive, and so only the dimmer background is shown at their locations, which are marked by dotted borders. At time 0.25 seconds a different random selection of stimuli from a right hemifield family of stimuli is displayed, again, only to the left eye. The opaque wall material of FIG. 2 blocks the right eye from seeing any of the stimuli for the left eye. At time 0.5 seconds the right eye receives its first stimuli. In this example (and others described herein), the time steps are 0.25 seconds, but it will be understood that a different time step may be used. The order of hemifield families that may present active stimuli, so-called volleys, then repeats through 8 steps per round-robin cycle. It will be understood that, by selection of different families of stimuli, there could be fewer or more time steps per cycle. The figure shows a possible set of stimuli as presented over three of these round-robin cycles from row A to X.

FIG. 10A at top shows the 44 estimated response waveforms, each a different shade of grey, one for each of the 44 stimuli of the P129 stimulus array. Each waveform is the weighted sum of two basis-function wave forms. FIG. 10B are the 44 weighted versions of the first basis-function, which are response components based on basis-function 1. FIG. 10C are weighted versions of the second basis-function which are response components based on basis-function 2. Thus, the sets of 44 pairs of response component waveforms in FIGS. 10B and 10C are summed to give the estimated responses in FIG. 10A.

FIG. 11A are the median responses obtained with gain-kernels estimated, and FIG. 11B without gain-kernels estimated.

DETAILED DESCRIPTION

Figure 1:
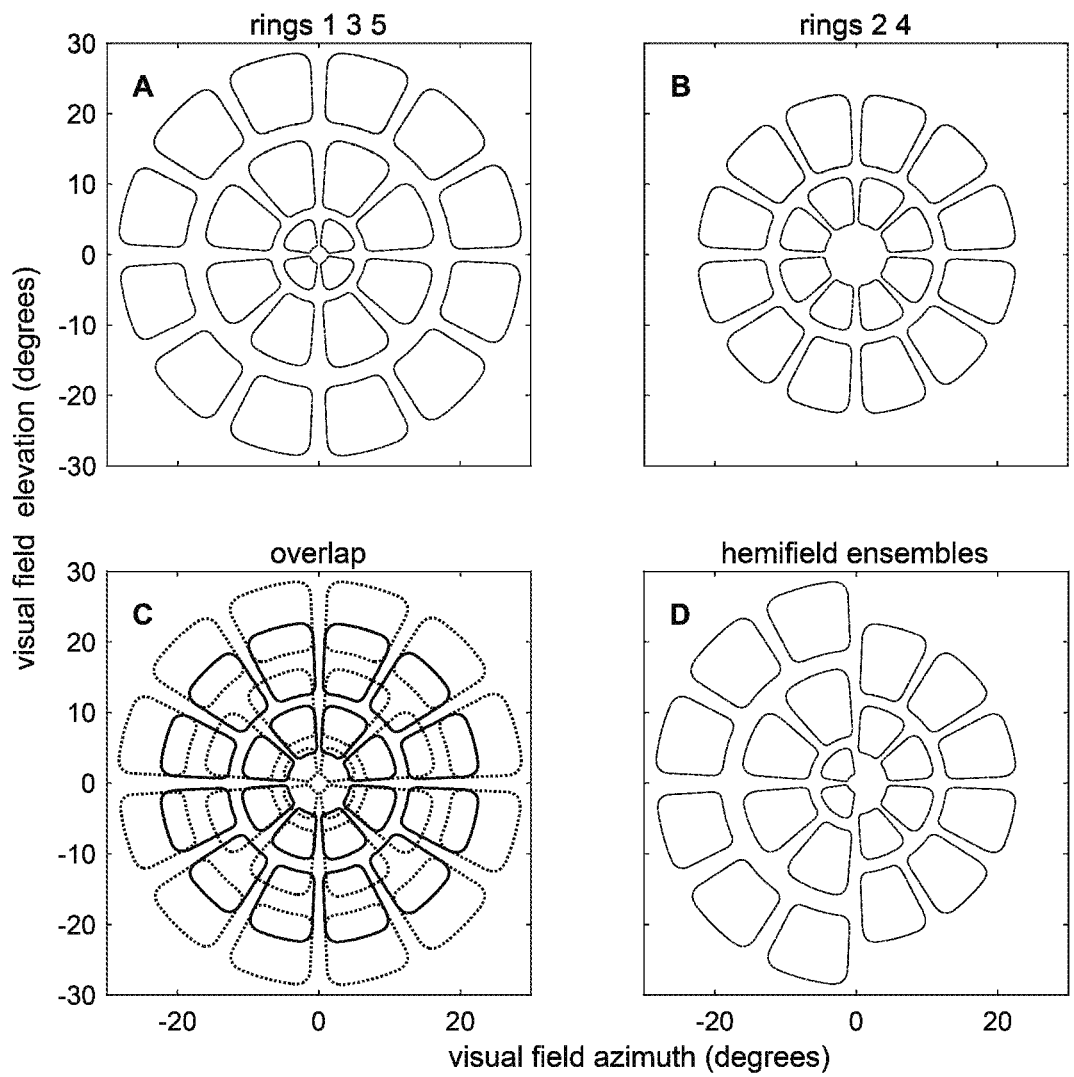
FIG. 1 shows the layout of a set of 44 multifocal stimuli that tile the central 60 degrees of a visual field of a test subject when they fixate the center of the array. Each lozenge-shaped enclosed contour represents the outer boundary of one stimulus. When indicated by the controlling stimulus sequences, one or more of the stimuli adopt their active state for some period. In this particular non-limiting example, each active region is filled with bright yellow light for 33 ms, and the background is a much dimmer yellow. The 44 stimuli can be segregated into three (A) or two (B) sets of non-overlapping rings. If the set of 44 stimuli were all active at the same time they would overlap as shown in (C). The 3-ring or 2-ring sets can be further divided into families either tiling a left or right hemifield, alternatively, as shown in (D).

FIG. 1 illustrates an array of 44 multifocal stimuli for presentation to the eye of a person or animal. Each stimulus (i.e. stimulus element) is lozenge shaped. Here only the outer edges of the stimuli (i.e. stimulus elements) are shown as black enclosing lines. In this particular non-limiting demonstration every part of a lozenge-shape stimulus region is bright yellow and is briefly presented on an unchanging dimmer background. During a test the subject stares straight ahead at the center of the array of stimuli, fixing their eyes on a small red cross located there. In the case of an animal they may be anesthetized. At the beginning of the test there are no stimuli, only the background. When the test starts, stimulus sequences determine when a given stimulus appears at its location. Each yellow stimulus is presented for 33 ms each time the stimulus sequence calls for its presentation. Over the course of the test any given region has a low probability of appearing in a pseudo-random fashion. That randomness is required for the multifocal method to work, because it keeps presentation of stimuli at one region statistically independent of stimuli presented at other regions. That is, on any time step, each individual stimulus element has a probability of being presented of about 50%. The stimuli are arranged in 5 rings, which are shown in FIGS. 1A, 1B. Although overlapping regions are never displayed together, the way they would overlap if presented at the same time is shown in FIG. 1C. Examples of left and right hemifield-sets, or families, of either the three rings of FIG. 1A, or the two rings of FIG. 1B are shown in FIG. 1D. As the axis labels indicate the array of 44 stimuli extend to 30 degrees of the visual field from the central fixation point.

Figure 2:
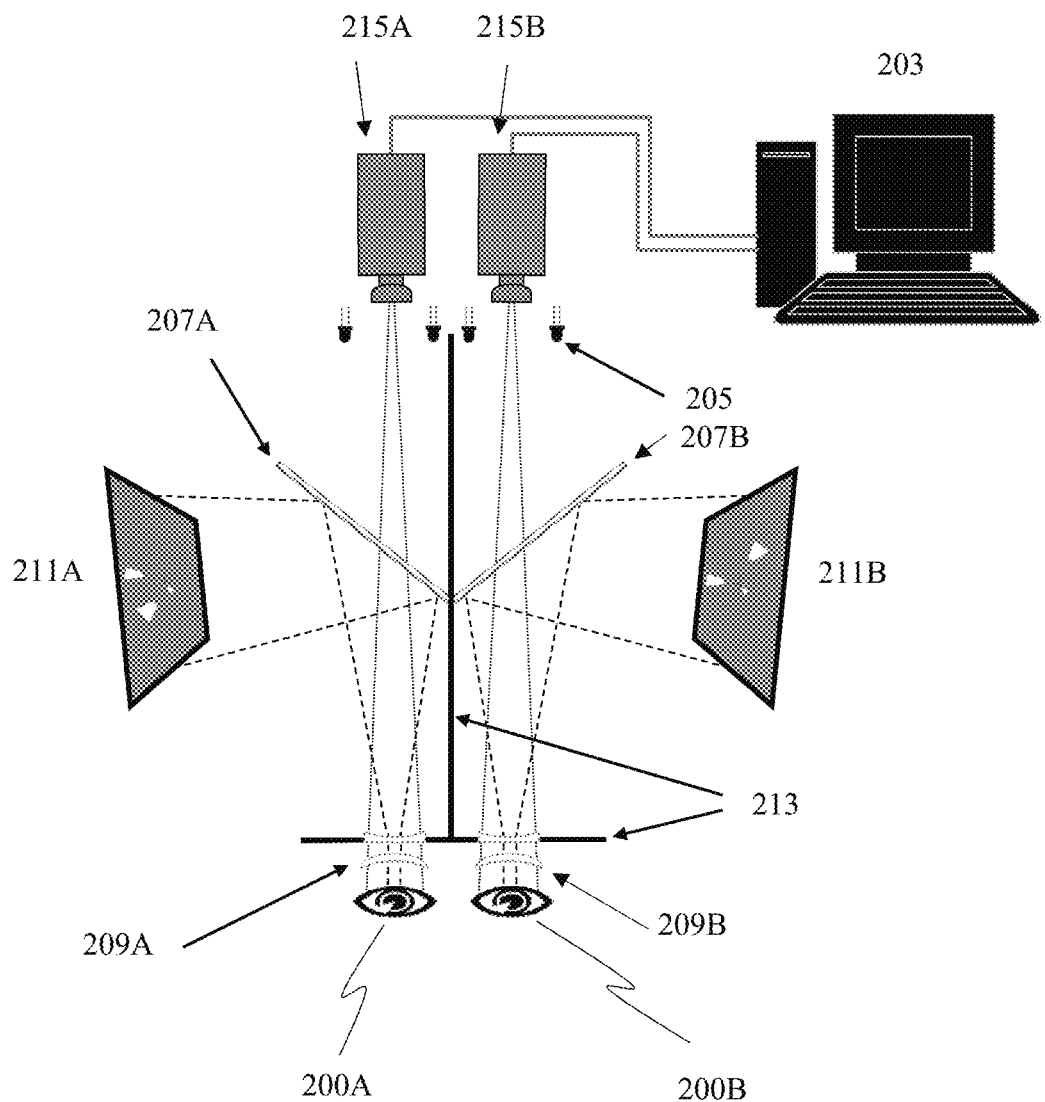
FIG. 2 illustrates an apparatus for: 1) presenting separate multifocal stimuli to the two eyes separately; 2) obtaining video records of the two pupils under infrared illumination; and 3) a computerized system for controlling the display of the multifocal stimuli on the two display systems, coordinating the video capture of images of the pupils with the stimuli, and estimating (i.e. measuring) the individual responses to the stimuli presented at each of many locations.

In fact, there can be two concurrently presented arrays of stimuli, 44 for each eye. FIG. 2 shows that these are presented concurrently to the two eyes (200A, 200B) using a non-limiting stereoscopic arrangement. FIG. 2 shows a computer system 201 with a computer 203. A light source 205, such as an infrared light source for example, is controlled by the computer 203. The eyes of the subject are illuminated with infrared light from the light source 205 through a pair of cold-mirrors (207A, 207B), the cold-mirrors being transparent to infrared light. The cold-mirrors work normally for visible light and so using them, and the objective lenses (209A, 209B), allows each eye to see one of two display systems (211A, 2111B), each display system presenting a multifocal array of stimuli as, for example, in FIG. 1 to each eye. Opaque walls (213) isolate the left and right halves of the apparatus so that the eyes cannot see the opposite side. The display systems (211A, 2111B) also contain visual cues, which cause the subject to automatically binocularly fuse the images displayed on the two display systems. The subject is therefore unaware that they are viewing two images, one being displayed on each of the two display systems, instead they perceive that they are looking at a single image. Two sensors (215A, 215B) in the form of infrared video cameras, for example, capture moving pictures of the pupils and the computer 203 of the computer system 201 continuously measures the pupil diameter to provide a temporal record of pupil response to the multifocal stimuli. The computer 203 of the computer system 201 implements a response estimation (or calculation) method using the 88 stimulus histories, i.e. the display sequences used, and the pupil responses in order to estimate (or measure) the temporal impulse responses to each stimulus sequence and a set of gain-kernels.

FIG. 3A illustrates a set of 176 estimated temporal impulse response waveforms, 44 from each eye and pupil. Downward deflection of the waveforms indicates a decreased pupil diameter. FIG. 3B shows the peak amplitude of constriction and the time to that peak constriction, the time-to-peak, which is estimated for each impulse response. The time-to-peak provides a measure of response delay. In conventional visual field testing, sensitivity is estimated by modulating the stimulus over a decibel scale; herein the μm constrictions shown here are later converted to decibel amplitudes to yield sensitivity.

Figure 3:
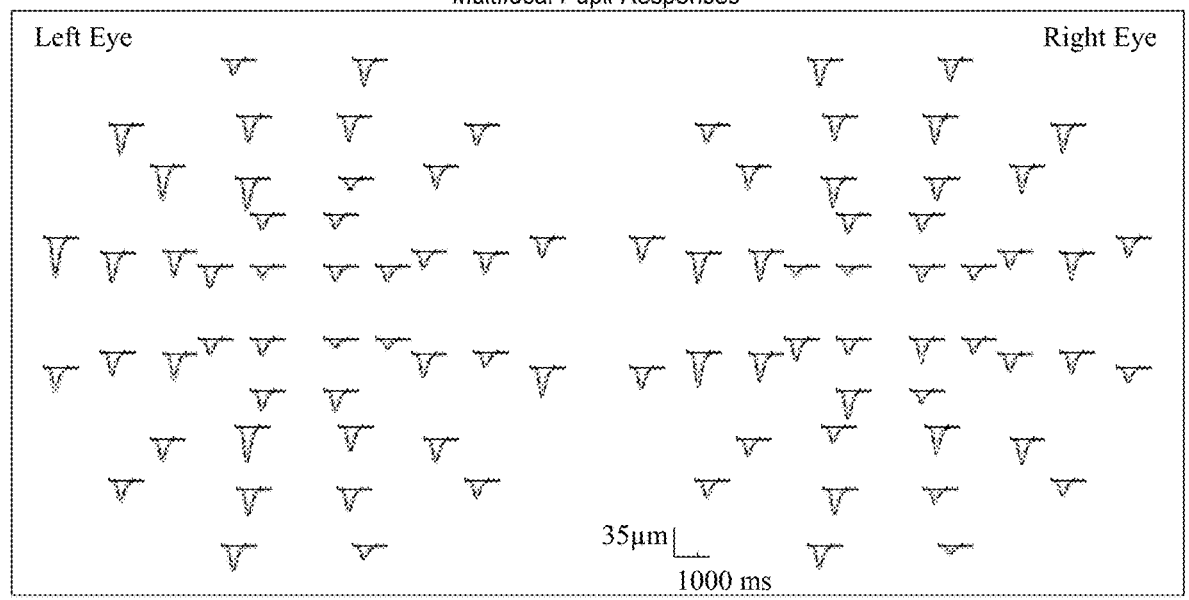
FIG. 3 shows 176 temporal impulse responses, also called linear weighting functions, which are the average responses of the pupils to presentations of each of 44 stimuli per eye as illustrated in FIGS. 1 and 2. In (A) there are pairs of impulse response waveforms corresponding to the location of the stimulus that evoked them, following the layout of the stimuli in FIG. 1. There are two waveforms for each stimulus location because, as indicated by the legend, one is sourced from the response of the left pupil, and one from the right. This comes about because, as shown in FIG. 2, both eyes were stimulated and both pupils recorded concurrently. Each pupil receives information about stimulation of each eye. As indicated by the inset axes in (A), each plot begins at the stimulus presentation time 0, and shows the time evolution of the responses over 1000 ms. The vertical scale is 35 μm and downward deflection of the waveforms indicates decreasing pupil diameter. Thus, the average response to the pseudo-randomly flashed stimuli is a brief, smooth, pupil constriction followed by a slower recovery to baseline diameter. Both the amplitude and time to peak of each waveform can be estimated as indicated in (B).
Figure 3:
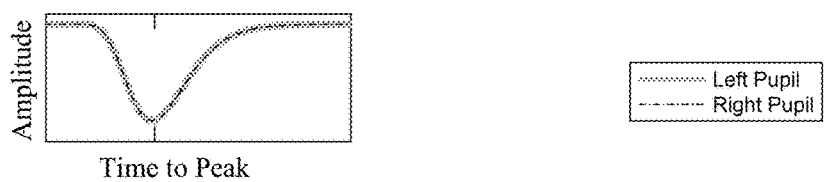
Figure 4:
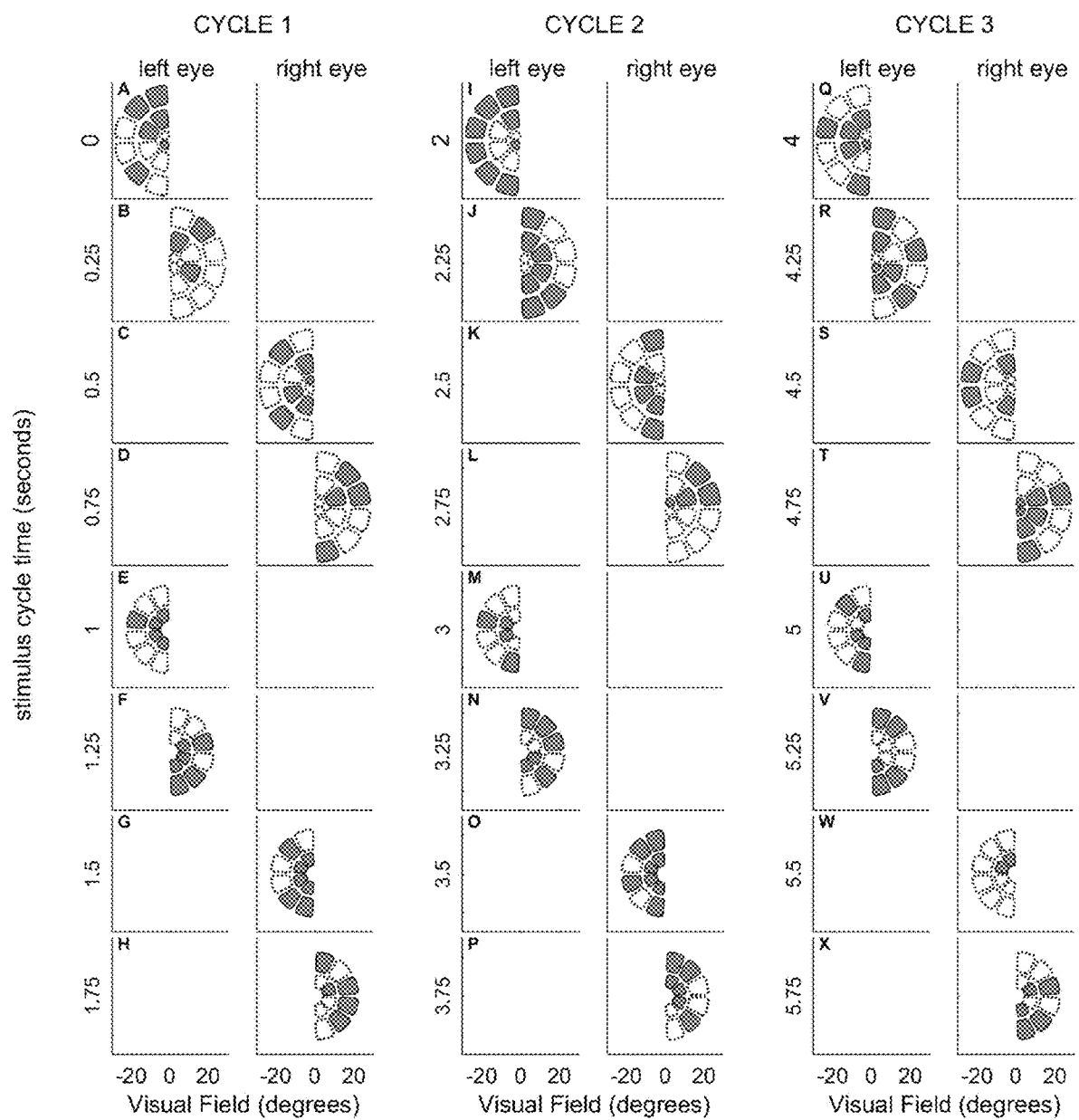
FIG. 4 illustrates three of many cycles of multifocal stimulation of the two eyes using an apparatus like that described in FIG. 2. The CYCLE 1 column shows that at time 0, six of the stimuli (stimulus elements) from a left hemifield family of stimuli (e.g.

FIG. 4 illustrates how in a particular non-limiting example that yielded the responses of FIG. 3, the 88 stimulus sequences were combined to present the stimuli in randomized clustered-volleys. Time in seconds proceeds from top to bottom down each of columns 1 to 3. There are pairs of panels on each row of a column. Each pair of panels shows the stimuli presented to the left or right eye (column headings) via a system like that shown in FIG. 2. At intervals of 0.25 seconds, some of the possible stimuli within a hemifield family are presented as bright yellow for 33 ms. The presenting stimulus regions are shown as solid grey here. The figure demonstrates that about half the possible regions of a hemifield family, as in FIG. 1D, are not shown, and the dotted borders show where those other stimuli of each hemifield family would have appeared. Thus, at the beginning of the test, time 0 (A), six members of the family of the left hemifield stimuli are potentially activated for the left eye. At 0.25 seconds, about half the possible regions within the right hemifield family are active (3 in this case), and presented to the left eye. At 0.5 seconds, a new volley of left hemifield stimuli is presented to the right eye. This continues over time until 1.75 seconds when 1 cycle of the stimuli has been completed. The sequences of hemifield families then repeat every 2 seconds in a round-robin fashion, as shown in rows I to X of CYCLES 2 and 3, but on each time step any member region of the family has a 50% chance of being active, i.e. of being presented. This randomized presentation of individual regions keeps the stimulus sequences statistically independent to allow a multifocal response estimation method to extract the responses from the pupil records. In this example, the cycles repeated until every stimulus region was presented 96 times, requiring 6 minutes in total. Sometimes other sets of families are used (see below) and different numbers of repeats per region are used. Different numbers or colors of stimuli may also be used.

Continuing with the current example stimuli however, it can be seen that the sets of hemifield families can be assigned to different sorts of symbolic stimulus groups. The purpose of these groups is to reduce the number of estimated gain-kernels further from the full set of possible gain-kernels; one for each hemifield family. Each family is assigned to a particular group and these have a common gain-kernel. Thus, the number of coefficients that are required to be estimated is fewer. There is, however, a risk that too many, or the wrong, families will be assigned to particular symbolic analysis groups resulting in poor overall estimates. That is to say, incorrect assignment of the groups may fail to capture important features of the dynamics of the pupillary nervous system. Efficient and advantageous symbolic groups were discovered by experimentation.

Figure 5:
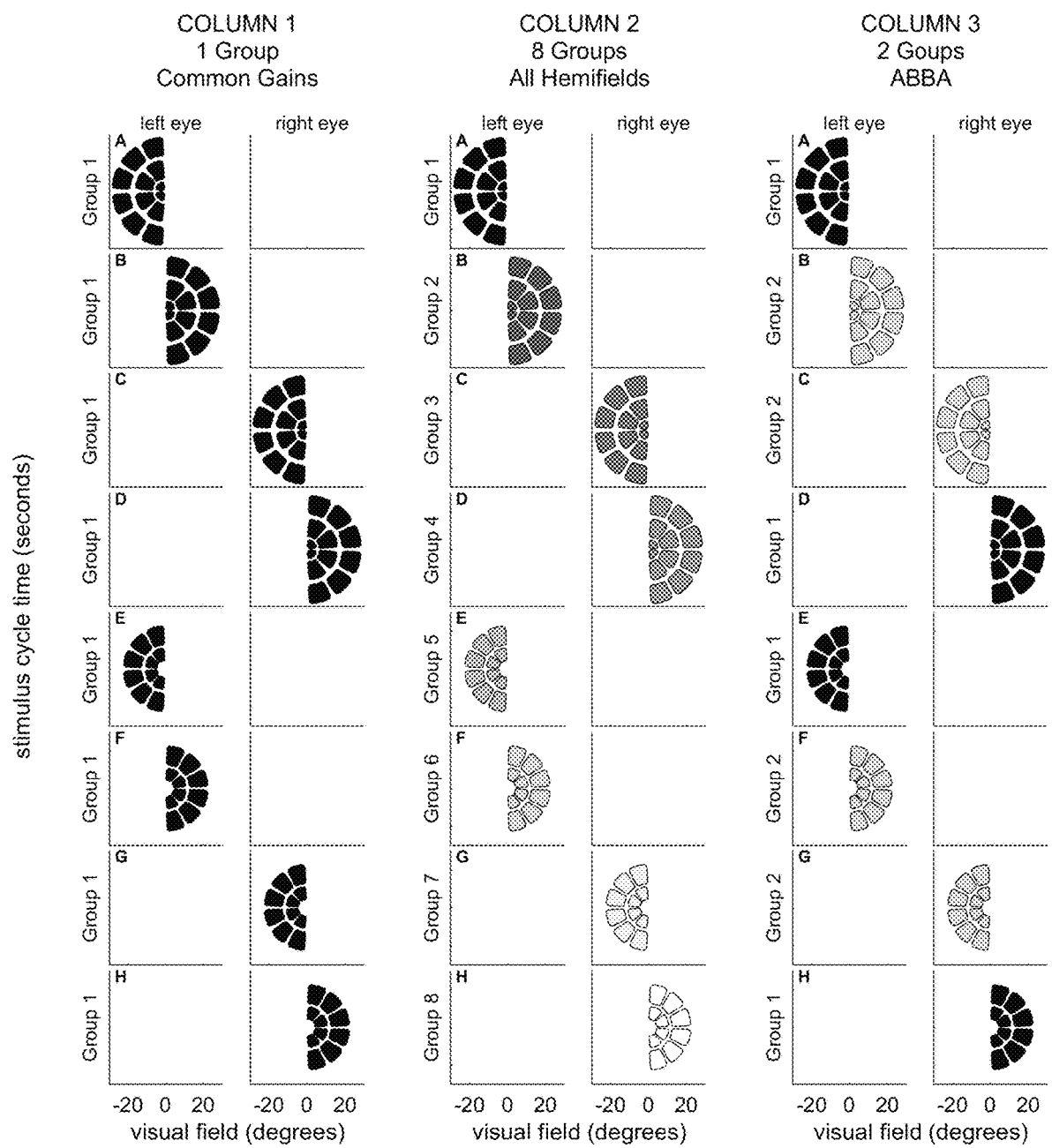
FIG. 5 shows three possible allocations of one cycle of a clustered-volleys multifocal stimulus like that of FIG. 4 into symbolic stimulus groups. Once groups are assigned they are maintained over the multiple round-robin cycles of the whole stimulus. COLUMN 1 on the left shows all the stimulus families colored black indicating they all belong to one symbolic group (ordinate labels of A to H). COLUMN 2 shows an assignment of families to 8 separate symbolic groups (shown in black, grey (from dark grey to light grey) and white, and ordinate labels of A to H). In COLUMN 3 the hemifield families are assigned to two groups: black or light grey (and ordinate labels on A to H), according to the repeated pattern ABBA. These types of group assignments are used by the herein described response estimation methods to reduce the number of gain-kernel coefficients required to characterize dynamic changes in pupil responsiveness. That is, only one gain-kernel per symbolic stimulus group is estimated (i.e. measured), each for some number of time steps, or lags, in the stimulus histories. By selecting groups that capture important features of the pupillary nervous system, and estimating (i.e. measuring) gain-kernels for stimuli belonging to those groups, accurate multifocal responses can be efficiently estimated.

FIG. 5 illustrates three possible symbolic group assignment methods. In this figure each column represents a different group assignment strategy that would repeat on every cycle of the full test sequence. In the left COLUMN 1 (comprising rows A to H) all the hemifield families are colored black indicating they will all be treated as a single group for response estimation. That is a single gain-kernel (i.e. a set of gain-kernel coefficients) will be estimated for all of them, hence this method is referred to as Common Gains. In the central COLUMN 2 every hemifield family is colored black, one of six grey scales from dark to light or white indicating that each is treated as one of 8 groups for response estimation. That is a different gain-kernel will be estimated for each of the 8 symbolic groups, and hence is referred to as the All Hemifields method. In COLUMN 3 the hemifield families are assigned to one of two groups in the order ABBA, ABBA, etc, for the duration of the stimulus. In this figure and FIG. 6 the ordinate labels for each row reflect the group assignments: Group 1, Group 2, etc. Those assignments will be maintained for all cycles of the stimulus.

Figure 6:
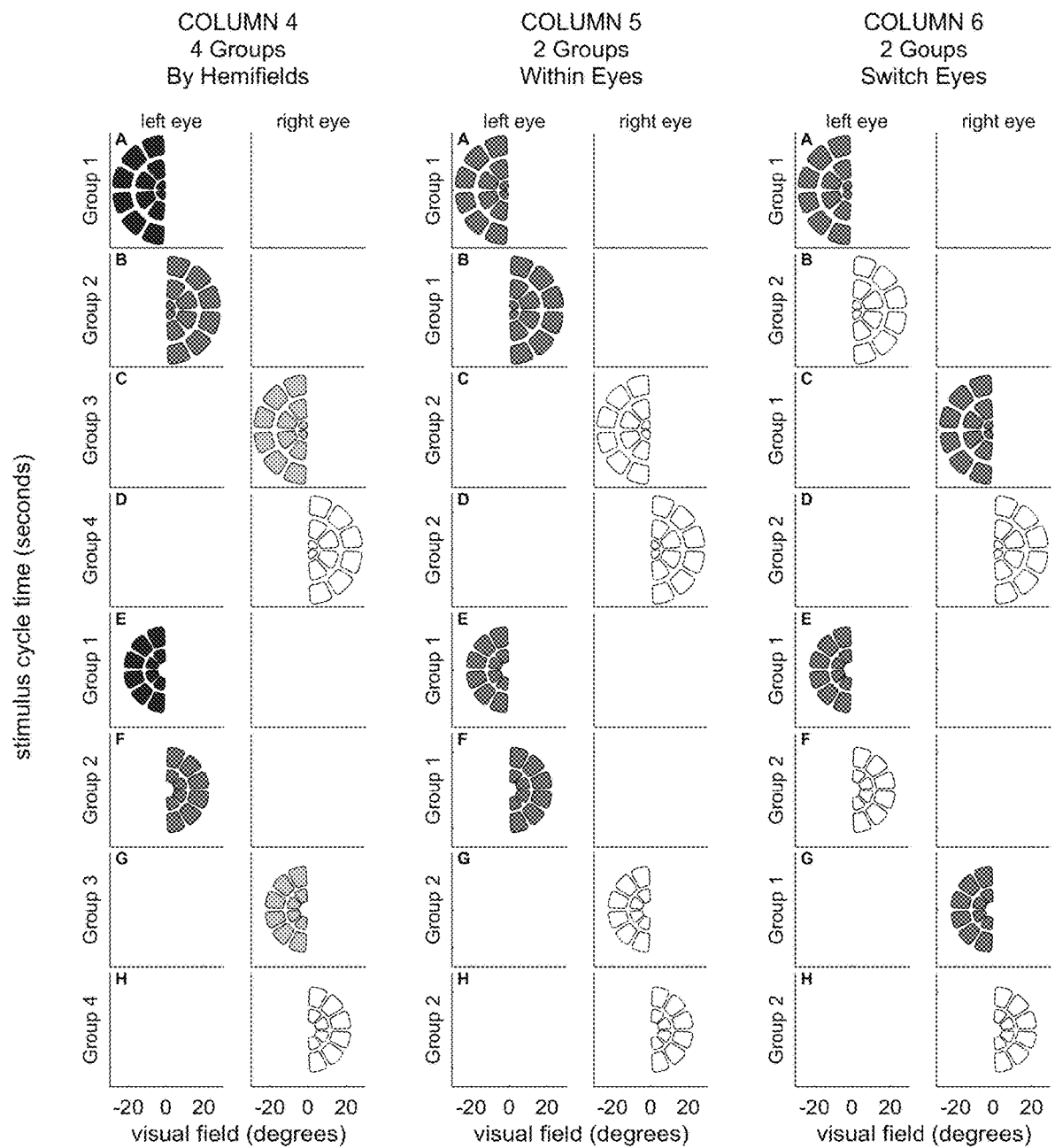
FIG. 6 Illustrates three alternative assignments of clustered-volleys into symbolic stimulus groups. COLUMN 4 shows four groups being assigned regardless of whether they belong to the larger 3-ring, 12-stimulus hemifield families, or the smaller families of 10 stimuli arranged in 2 half-rings. COLUMN 5 shows an assignment into two symbolic groups (shown by the grey and white colorings and the ordinate labels on A to H) in which the groups are defined by the eye being presented to. COLUMN 6 shows an assignment into 4 symbolic groups that are defined by larger and smaller hemifield families and stimulated eyes, such that the group assignment switches eyes on every second time step, hence is referred to as the Switch Eyes assignment method.

FIG. 6 shows three further alternative assignments of symbolic groups. In COLUMN 4 (A to H) there are four symbolic stimulus groups, assigned to 1 to 4 for the 3-ring stimuli of rows A to D, and then repeated for the similar 2-ring stimuli in rows E to H. The assignments are thus referred to as the By Hemifields method, regardless of whether the hemifield families have 2 or 3 rings. The central COLUMN 5, shows an assignment to two groups (dark grey and white, and ordinate labels) that correspond to the stimulated eye. Hence the assignments are referred to as the Within Eyes method. In the right COLUMN 6 the hemifield families are assigned into 2 groups (the grey shade or white, and ordinate labels). The assignments always switch to the like-hemifield in the opposite eye, and hence this assignment to symbolic stimulus groups is referred to as the Switch Eyes method.

Figure 7:
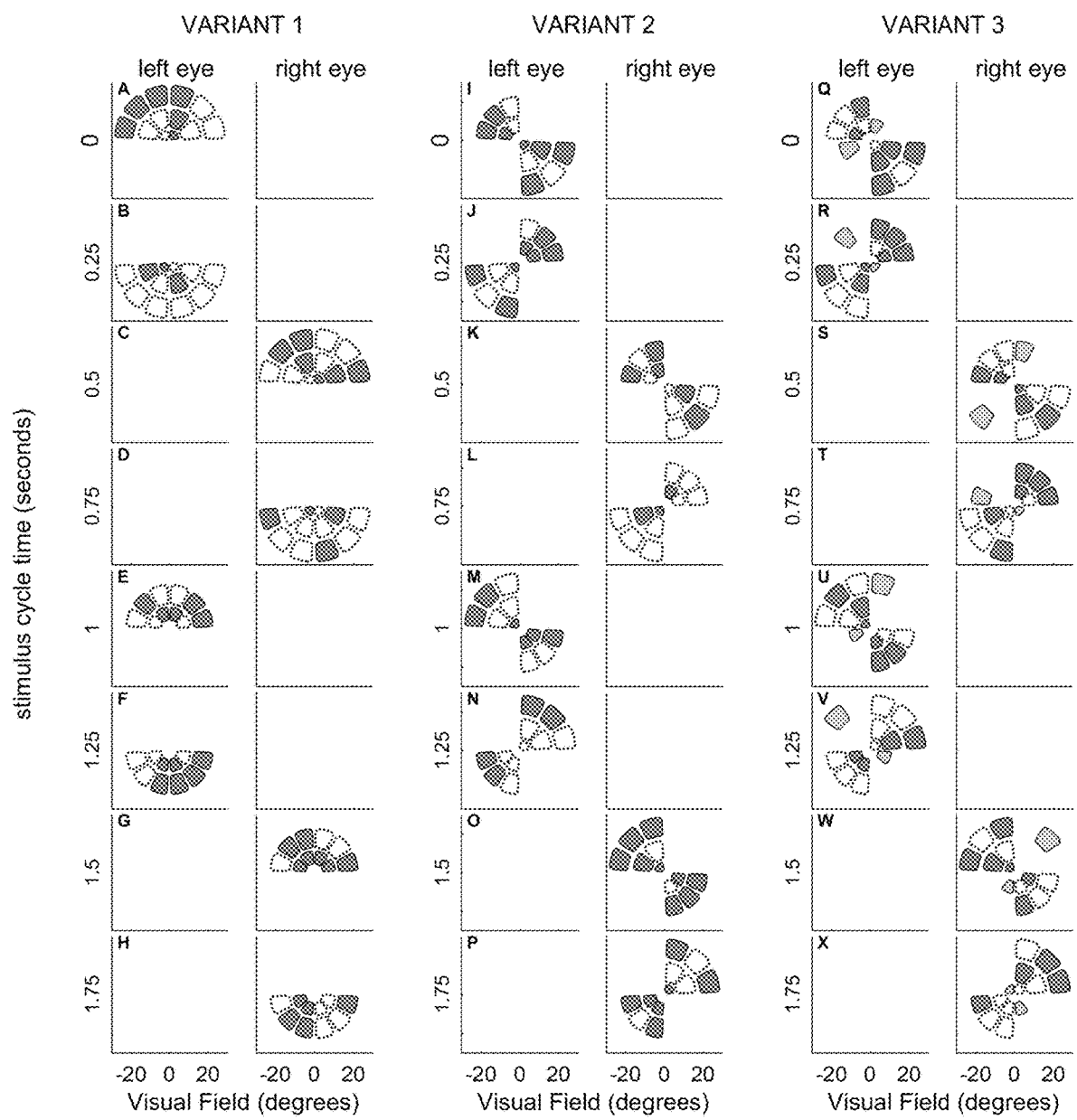
FIG. 7 Illustrates clustered-volley methods that use different types of families of stimuli that cycle in a round-robin fashion as those in FIG. 4. Here the families are: VARIANT 1, superior versus inferior hemifields; VARIANT 2, alternating quadrants; and VARIANT 3, alternating quadrants with sporadic extra stimuli in other quadrants (light grey).

Thus far the examples all had families that were collections of stimuli from either the left or right hemifield. Alternative types of families may also be used, some examples being illustrated in FIG. 7. Each column of FIG. 7 shows different types of families that would repeat in a round-robin fashion as in FIG. 4. As in FIG. 4, different stimuli from within each family are active at random (grey regions). The left-most column, VARIANT 1 (Rows A to H), uses families that are arranged in hemifields, but inferior and superior hemifields rather than left versus right. The central column, VARIANT 2 (rows I to P), illustrates families that are alternating pairs of quadrants. To this point the families have comprised regular subsets of stimulus regions. The third column of FIG. 7, VARIANT 3 (rows Q to X), is similar the central VARIANT 2 but occasional sporadic extra regions appear in VARIANT 3. To make it clear which are the sporadic extra regions they are presented in a lighter shade of grey. In practice they could be the same or similar brightness and color to the other stimuli. VARIANT 3 illustrates that irregular families are possible, where different degrees of departure from regular patterns of families could be tolerated. It is clear that the rows of FIG. 7 could be assigned to symbolic stimulus groups like those in FIGS. 5 and 6 or other groups.

The examples show the methods (and associated system) described reduce the number of gain-kernels that are required to be estimated, while at the same time increasing the accuracy of the impulse responses obtained from each stimulus region that are estimated together with the gain-kernels.

Embodiments of the invention have been developed primarily for use as methods and systems for quantification of the visual fields by estimating responses of the visual nervous system from recordings of pupil size over time obtained in response to multifocal stimuli. Embodiments include methods and systems for quantifying stimulus-dependent dynamic changes to the pupillary system, i.e. dynamic changes in pupil response gain. Dynamic changes in pupil response gain that are measured by small sets of coefficients are termed "gain kernels" in this document. This is a departure from only estimating linear and non-linear weighting functions to characterize systems containing non-linearities. In principle there can be one gain-kernel for every stimulus sequence but instead they are estimated for smaller symbolic groups of stimulus sequences. Thus, if 88 stimulus sequences were divided into 8 groups then only 8 gain-kernels will be estimated, not 88. If the stimuli are summarized by 2 symbolic stimulus groups, then only 2 gain-kernels are required be estimated. Estimation of gain-kernels for limited numbers of symbolic stimulus groups had not been thought of or attempted before. Aside from estimating gain-kernels, embodiments are based upon the discovery that particular symbolic stimulus groups are surprisingly advantageous.

Described above are some features of particular non-limiting types of multifocal stimuli. These display pseudo-randomly presented stimuli to 44 regions of the visual fields of each of the two eyes, as illustrated in FIGS. 1 and 2. The stimuli were delivered in so-called clustered-volleys as illustrated in FIG. 4. Under that scheme one of a set of 8 families of stimuli that are distributed in left or right hemifields of the left or right eye are selected for possible presentation on each 0.25 second interval. The sequence of 8 hemifield families repeats in a round-robin fashion. FIG. 4 shows three cycles of this repeated process. On any one 0.25 second time step each stimulus region of the hemifield family has a 50% chance of being active, that is of the stimulus region being presented as bright yellow within its lozenge shaped boundary, presented against a dimmer background. The total stimulus duration is 383 seconds and over that period each of the 88 stimulus regions is activated 96 times. When presented each stimulus remains bright (active) for $\frac{1}{30}$ of second (33 ms). Activations of each of the 88 regions are controlled by 88 stimulus sequences, also called stimulus sequences or stimulus trains. These consist of 0s and 1s as shown in FIG. 8A. A stimulus is activated, i.e. presented for 33 ms, when the sequence changes from 0 to 1. The interval of the time steps of stimulus sequences, i.e. their temporal resolution, is $\frac{1}{30}$ of a second. The volleys of stimuli appear on average at every 0.25 seconds.

The pupil response is a continuous record of the pupil diameter captured over time in synchrony with the stimulus presentations. The pupil diameter responds to the sum of all the activity generated by the stimuli presented to the two eyes. The pupil diameter contains this information because it is conveyed to the irises from the Pretectal Olivary Nuclei (PON), which receive input from the extra-striate visual cortex and the retina. The two PON each provide information from both eyes to both Edinger-Westphal Nuclei each of which innervates one iris, thus each iris responds to stimulation of both retinas. The stimulus sequences and pupillary light response record are then submitted to a regressive response estimation method or system, to extract the responses of the visual system to each of the 88 stimulus regions. There are two pupil records, one from each eye, so the response estimation process will be repeated twice to yield a total of 176 estimated responses. FIG. 3A shows a set of 176 linear weighting functions, i.e. average temporal impulse responses, that are the result of a standard regressive response estimation process.

Figure 8:
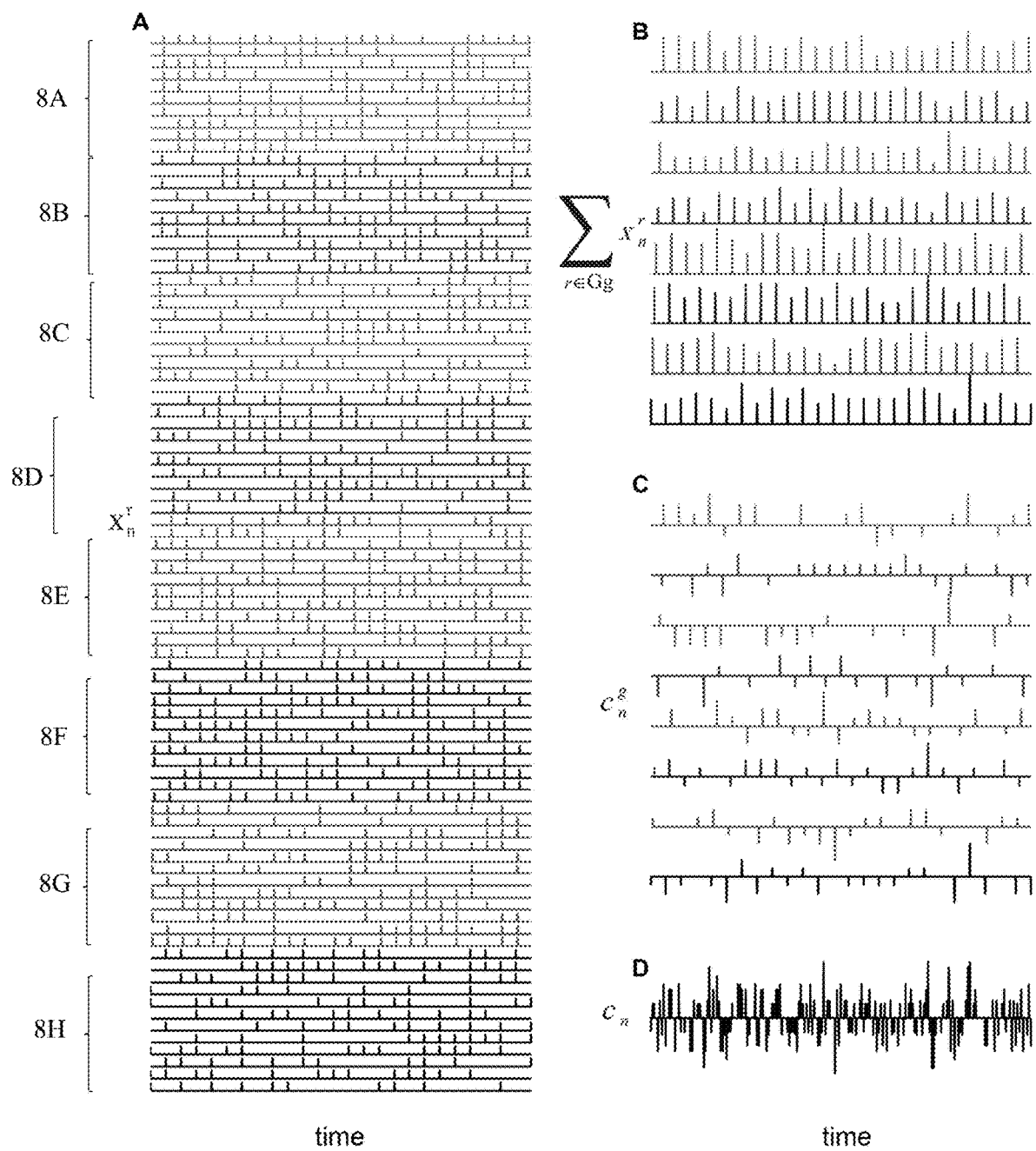
FIG. 8 Shows four steps in the transformation from the 88 controlling stimulus-presentation sequences, $x_n^r$, for each region r and 0.25 second time step n into the relative contrast parameter $c_n^g$ for each symbolic group g, and its summed version $c_n$. These are the inputs to estimating the coefficients of symbolic stimulus group g's pupil gain-kernels, $h_j^g$ for each time lag j. In (A) the stimulus-presentation sequences have been blocked into 8 symbolic stimulus groups (denoted by 8 the grey colorings and depicted by sections 8A to 8H), corresponding to the groups of FIG. 5 COLUMN 2. Only the first 50 seconds of the 240-second long sequences are shown. In each sequence of A, an upward tick indicates that a stimulus is presented at one of the 44 regions per eye. FIGS. (B) and (C) show the steps of computing Equation 1. D shows the sum of equation 1 over groups: $c_n$.

Recent research had provided evidence that the pupillary system does not remain linear, however, and so incorporated into the response estimation process is a method to capture nonlinear dynamics in the form of gain-kernels. FIG. 8 shows the steps in an illustrative process. FIG. 8A shows the first 50 seconds of the 88 stimulus sequences used to produce the responses of FIG. 3. There is one sequence per stimulus region, 44 per eye as in FIGS. 1 and 4. The horizontal lines of FIG. 8A are sequences of 0s, and the occasional upward tick is a 1 indicating that a stimulus should be presented. In this non-limiting example, the stimulus sequences are presented in 8 blocks of different grey tones. These represent the 8 symbolic stimulus groups of FIG. 5 COLUMN 2. Strictly speaking, groups 1 to 8 of FIG. 5 COLUMN 2 go up the page in FIG. 8 with the 12-region per hemifield families at the bottom, and the 10-region per hemifield families at the top.

Signals were developed that represent the dynamic balance of stimulation over time within a group to quantify any fluctuation in stimulus strength within a group. These will be used in a regressive framework to add the estimation of coefficients of so-called gain-kernels to the standard process of estimating the coefficients of the impulse responses from each stimulus. The process starts with the stimulus sequences of FIG. 8A that are labelled $x_n^r$, indicating the stimulus sequence for region r at time step n. That is, the input indicating stimulus activity at $t=t_n$ for region r is denoted $x_n^r$, for $n=1, \ldots, n_t$, where $n_t$ is the number of time steps. If the times at which the volleys occur are defined as $t_i = t_{k_0}, t_{k_1}, \ldots, t_{k_p}$, then the value of $x_n^r$ is 1 when a flash occurs ($n \in k_0, k_1, \ldots, k_p$) and is otherwise 0 (FIG. 8A). The value 0 represents a dimmer background level. If $\bar{x}^g$ is the median number of regions chosen from the symbolic stimulus group g and $G_g$ is the set of regions in group g, then the relative contrast parameter at time $t_n$ can be defined as:

$$c_n^g = \frac{\left(\sum_{r \in G_g} x_n^r\right)}{\bar{x}^g} \quad (1)$$

for $n \in k_0, k_1, \ldots, k_p$ and otherwise 0. Note that $G_g$ is the gth symbolic stimulus group of a set like any of those in FIGS. 5 and 6. FIG. 8B shows the summation step: $\Sigma_{r \in G_g} x_n^r$, and FIG. 8C the outputs of Equation 1 above, $c_n^g$. Note that $c_n^g$ gives a measure of the relative instantaneous balance of stimulation relative to the median level defined by the frequency of stimuli within the groups. Thus, $c_n^g$ is positive when the number of stimuli is greater than average in that group and negative when there are fewer. For the example stimuli, only random selections of the stimuli in a single group are displayed at any time and thus a single vector can be formed representing the stimulus contrast at each time $t_n$: $c_n = \Sigma_{g=1}^8 c_n^g$ for $n=1, \ldots, n_t$, as shown in in FIG. 8D. Having provided that framework a temporally integrated contrast parameter is introduced for each group ($\bar{c}_n^g$) that depends on the current and past values of $c_n$ (FIG. 8D) at the points where for $n \in k_0, k_1, \ldots, k_p$ (where the stimuli occur):

$$\bar{c}_{k_i}^g = \sum_{j=0}^{M_g} h_j^g c_{k_{i-j}}, \quad (2)$$

and otherwise is 0 ($i=0, 1, \ldots, p$). Here $h_j^g$ is the pupil gain-kernel for group g and $M_g$ is the number of steps after which gain changes become insignificant, i.e. when dynamic changes in responsiveness become trivial. Thus, $M_g$ is the number of temporal lags in the stimulus history of a group, i.e. the stimulus sequence of a group, that are required to be considered to capture the effects of dynamic gain changes, i.e. the number of lag-coefficients per kernel. The time between two of the entries of $h_j^g$ at j+1 and j is $(k_{i-j}-k_{i-j-1})/30$. In reality, the entries of $h_j^g$ are separated by 7 or 8 steps of 1/30 second, depending on the group, and, so on average, represent 0.25 seconds. The pupil gain-kernel is thus a sparse description of how current (j=0) or previous (j>0) values of $c_{k_i}$ are summated in time. Equation 2, $\bar{c}_{k_i}^g$, is therefore a measure of how much stimulus has recently been delivered depending on the temporal integrative properties of the pupil described by the gain-kernel $h_j^g$.

A divisive normalization factor for symbolic stimulus group g is defined as $$\gamma_i^g = \frac{1}{1 + \bar{c}_i^g}$$

(for $i \in k_0, k_1, \ldots, k_p$, and is otherwise 0), which is approximated using Taylor's theorem:

$$\gamma_i^g = 1 - \bar{c}_i^g. \quad (3)$$

for $i \in k_0, k_1, \ldots, k_p$. If new inputs are defined for each group g, $\check{x}_n^r = \gamma_n^g x_n^r$ for $n=1, \ldots, n_t$ and $r \in G_g$, the subscript can be dropped and the vector notation $\check{x}^r = \gamma^g \odot x^r$ can be used where ($\odot$) is the element-wise product. The component of the pupillary light response due to region r in group g at $t=t_n$ is modelled as:

$$f_n^r = \sum_{i=0}^M \varphi_i^r \check{x}_{n-i}^r \quad (4)$$

where M is the number of time steps after which the impulse response is not significant (~2 seconds or 60 timesteps of 1/30 seconds). The basis-functions $\varphi_i^r$ describe the temporal impulse response of the pupil at each region r, like the responses in FIG. 3. The basis-functions for each region can be modelled by the lognormal function:

$$\varphi_i^r = \varphi^r(t_i) = \frac{A^r}{\sqrt{2\pi}\,\sigma^r t_i} \exp\left(\frac{-\left(\left(\log(t_i/t_p^r)\right) - (\sigma^r)^2\right)^2}{2(\sigma^r)^2}\right) t_i > 0 \quad (5)$$

where $A^r$ is the amplitude, $t_p^r$ is the time-to-peak and $\sigma^r$ is the temporal width parameter of the rth region. These are reasonable models of the linear weight functions, i.e. the temporal impulse responses of FIG. 3. From Eq. 4, the total pupil light response at time $t_n$ is defined as $f_n = \Sigma_{r=1}^{n_r} f_n^r$. The equation relating the pupil diameter $y_n$ (μm) at time $t_n$ to the pupillary light response is the discrete equation:

$$y_n = f_n + \mu_n + \varepsilon_n \quad (6)$$

where $\mu_n$ is the nuisance signal and $\varepsilon_n$ is the error term. In practice the 382-second stimuli are too long for individuals to tolerate. Therefore the full sequences, $x_n^r$, are divided into 9 segments of just over 42 seconds duration. The 9 segment records are later connected back into a single full-length record for analysis. This means each of the 9 segments can have a different slope, a constant drift. The nuisance signal $\mu_n$ is modelled as separate constant drifts $(v_1, \ldots, v_9)$ for each of the nine stimulus segments and the error term $\varepsilon_n$ is modelled as:

$$\sum_{k=0}^{10} d_k \varepsilon_{n-k} = z_n \quad (7)$$

where $d_0 = 1$ by convention. Note that here the k are in real time steps of 1/30 of second and in this non-limiting example 10 was considered. Thus, $\varepsilon_n$ is the result of an autoregressive process with white noise innovations $z_n$. The filter $d = [d_0, \ldots, d_9]$ is referred to as a pre-whitening filter. If the vectors $E = [\varepsilon_1, \ldots, \varepsilon_n]$ and $Z = [z_1, \ldots, z_n]$, are defined and D is the circulant matrix of d then Eq. 7 can be rewritten in matrix form as $DE = Z$. In other words, pre-whitening can be written as a matrix multiplication, the notation used below.

Fitting the Data to the Model—Response Estimation

An important assumption in the underlying fitting process is that the innovations $z_n$ do not contain autocorrelations. Consider the one-step ahead predictor $$\hat{y}(t_n | t_{n-1}) = \hat{y}_n = \sum_{k=0}^{n_k} d_k F_{n-k} - \sum_{k=1}^{n_k} d_k \breve{y}_{n-k} \quad (8)$$

Where $\breve{y}_n$ is the measured pupil diameter at time $t_n$ and $F_n = f_n + \mu_n$. If it is defined that $$\tilde{x}^r = \begin{bmatrix} x_1^r \\ \vdots \\ x_n^r \end{bmatrix},$$

a column vector of the stimulus at region r, and the input matrix $X = [\tilde{x}^1 | \ldots | \tilde{x}^{n_r}]$ together with the parameter vector $\theta$ that contains all parameters of the model:

$$\theta = [A^1, \ldots, A^{n_r}, t_p^1, \ldots, t_p^{n_r}, \sigma^1, \ldots, \sigma^{n_r},$$
$$d_1, \ldots, d_{n_k}, h_1^1, \ldots, h_{M_g}^1, \ldots, h_1^{n_r}, \ldots, h_{M_g}^{n_r}, v_1, \ldots, v_9],$$

then $F_n$ is a function of X and $\theta$: $F_n = F_n(X, \theta)$, and $\theta$ has $n_p = n_r \times 3 + n_k + n_r \times M_g + 9$ parameters if the full model is used.

This demonstrates the power of the regressive framework in that $\theta$ contains the parameters of the impulse response basis-functions: $A^r$, $t^r$, $\sigma^r$; the coefficients of the autoregressive filter d, and the n per-lag coefficients of the gain-kernels for each group. Thus all these are fitted simultaneously, thereby partitioning the variance in the pupil record into its component sources. Thus, the SE in parameters like the amplitude of the responses at each stimulus region, is reduced. The model is greatly simplified by forcing common parameter values of the gain-kernels, $h_j^g$, for the selected small set of symbolic groups of stimulus regions. Accurate selection of groups is required however to produce good estimates with fewer gain-kernels and their coefficients.

The model is fitted to the pupil data by minimizing the sum of squares of the error: $\min_\theta \{\Sigma_{k=1}^{n_t} z_k^2 / (n_t - n_p - 1)\}$ using the Marquardt-Levenberg algorithm. This requires evaluating $\hat{y}_n$ $(n_t \times 1)$, its Jacobian $J(X, \theta)$ $(n_p \times n_t)$ and Hessian $H(X, \theta)$ $(n_p \times n_p \times n_t)$ at $X(n_t \times n_r)$.

Having developed this method for simultaneously estimating the basis-functions for each stimulus region, $\varphi_i^r$; and also gain-kernels, $h_j^g$, that characterize dynamic change in the system for selected symbolic stimulus groups; next were determined parsimonious numbers and arrangements of symbolic stimulus groups, and the number of significant gain-kernel lags per group, $M_g$ that produce improved response estimation.

The regressive frame-work can be summarized as follows. The class of standard methods for measuring, or in statistical jargon "estimating", the impulse-responses, i.e. basis functions, for each stimulated visual field regions can be summarized as Estimate of the Basis functions=function(pupil
response records,stimulus records) (a)

Equation a can be summarized as: the estimate of the basis functions and their scale that characterize the average response to the stimuli are a function of the pupil records and the stimulus records. Typically, there are one or two time-varying pupil response records from one subject from one recording session, and a number of stimulus records, as in FIG. 3A, describing the onset times and durations of stimuli for each tested part of the visual fields of one or both eyes. There may be more than one basis function per tested visual field region and the average per-region response in that case would be a linear or nonlinear combination of the per-region basis functions. Measurement of the basis functions can be done by a regressive method or cross-correlation. In the regressive framework the basis function estimation process can be improved by including other terms in the equation.

Estimate of Basis functions=function(pupil response
records,stimulus records,other terms) (b)

The $\theta$ of equation 8 describes the basis function term consisting of the coefficients to characterize the log-normal basis functions fitted: $A^1, \ldots, A^{n_r}, t_p^1, \ldots, t_p^{n_r}, \sigma^1, \ldots, \sigma^{n_r}$, and the other terms comprising the coefficients of the auto regressive model: $d_1, \ldots, d_{n_k}$; the coefficients of the gain-kernels $h_1^1, \ldots, h_{M_g}^1, \ldots, h_1^{n_r}, \ldots, h_{M_g}^{n_r}$ of which there are the number of symbolic groups times the number of time lags per group; and the nuisance terms for the nine segments, $v_1, \ldots, v_9$. Of course other terms could be added or different basis functions used as will be demonstrated below. The critical issue is to select the minimum set of symbolic groups and lags, i.e. the optimal gain-kernel coefficients, that together with the basis functions, minimize the sum of squares of the error. To allow the gain-kernels to be fitted the stimulus histories need to be transformed to the relative contrast parameters of equation 1, $c_n^g$, and its sum $c_n$, as shown in FIG. 8.

Bilinear Basis-Functions

As an alternate to the lognormal parametric form of the basis-functions, a general temporal impulse response $\varphi_i^r = h_i^r$ could be used, but this increases the number of parameters for the basis-functions to a point where the required test length would be too long. For example, 2 seconds would require 61 time points per region, increasing the number of parameters from 2 (amplitude and delay)×88=166, to 61 (time steps)×88 (regions)=5368. To keep test lengths reasonable one can assume that the waveform at each region is a weighted sum of l common temporal components ($\phi_i^j$):

$$h_i^r = \sum_{j=0}^{l} \alpha_j^r \phi_i^j \text{ for } i = 1, \ldots, M \tag{9}$$

Where $\alpha_j^r$ is the weighting factor of the jth temporal component in region r. Equation 4 can be replaced by the bilinear form as suggested by Goh, X. L., in her 2008 PhD thesis entitled: "Cortical generators of human multifocal visual evoked potentials and fields", DOI: 10.25911/5d51548ee0131:

$$f_n = \sum_{r=1}^{n_r} \sum_{i=0}^{M} \sum_{j=0}^{l} \alpha_j^r \phi_i^j x_{n-i}^r \tag{10}$$

If a single temporal component with 61 time steps is chosen then, in total, there are 61 (time steps)+88 (regions) =149 parameters, less than the lognormal parametric case, which has 177. For two components, there would be 298 basis-function parameters. The bilinear, gain, nuisance and autoregressive parameters can then be concurrently estimated using the Gauss-Newton method as suggested by Inverso, S. A., Goh, X. L., Henriksson, L., Vanni, S. and James, A. C., in their 2016 publication: "From evoked potentials to cortical currents: Resolving V1 and V2 components using retinotopy constrained source estimation without fMRI. Human brain mapping", volume 37, pp. 1696-1709.

Separated ON and OFF Channels

The contrast sequence $c_n^g$ can be separated, defined in Eq. 1, into its ON and OFF components $c_n^g = |c_n^g|^+ - |-c_n^g|^+$ where $|\bullet|^+$ is half wave rectification i.e. $|x|+=x$ when $x>0$ and is otherwise 0, that is, parts of $c_n^g$ that are positive (ON) or negative (OFF). Note that here ON and OFF refer respectively to positive and negative balances in the number of stimuli relative to the median number not to luminance contrast. If it is defined that the ON and OFF kernels for group g are $p^g$ and $q^g$, respectively, then Eq. 2 becomes:

$$\tilde{c}_{k_i}^g = \sum_{j=0}^{M_p} p_j^g |c_{k_{i-j}}|^+ - \sum_{j=0}^{M_q} q_j^g |-c_{k_{i-j}}|^+ \tag{11}$$

Here $M_p$ and $M_q$ are the number of steps after which gain becomes insignificant in the ON and OFF channels, respectively. Given the ON and OFF sequences are independent, the kernels for these two channels can be estimated. In the case where $p_j^g = q_j^g$ for all j, then the linear model defined by Eq. 2 with $h_j^g = p_j^g = q_j^g$ is recovered. Thus, Eq. 11 defines a broader class of models than Eq. 2.

Demonstration 1

To provide a data set with which to demonstrate the steps described herein 94 normal control subjects (43 male) aged 49.6±19.5 y (mean±standard deviation), range 18 to 91 y, and 40 persons who had one or both eyes affected by glaucoma, aged 67.2±8.60 y, range 50 to 83 y were tested. Glaucoma can cause localized damage to patches of retina producing changes in sensitivity and delay that may be characterized by making maps of visual function as provided by the current disclosure.

Each person was tested twice about 2 weeks apart with 3 variants of the clustered volleys multifocal stimuli (FIG. 4). For simplicity's sake the three test variants are referred to as P129, P130 and P131. The stimuli conformed to the 44 region/eye format of FIG. 1. P131 differed in that its array of stimuli were isomorphically reduced in scale by a factor of 2. Thus, the P131 stimulus samples a 4 times smaller area of the visual field but with 44 scaled stimuli per eye. The P129 and P131 stimuli were bright yellow on a dimmer 10 cdm$^{-2}$ background. The P130 stimuli were bright green on a 10 cd/m$^2$ red background. The stimulus intensities varied to achieve luminance balancing. The P129 stimuli range from 73 to 150 cd/m$^2$, P130 65 to 150 cd/m$^2$, and P131 134 to 288 cd/m$^2$. The individual test regions were presented pseudo-randomly such that each region presented a 33 ms stimulus at a mean interval of 4 s. The test duration was just over 6.3 minutes, and each region was presented 96 times. In every test both eyes were tested concurrently using an apparatus as in FIG. 2.

During the test the pupil diameters were recorded every 1/60 of a second in synchrony with the presentation of the multifocal stimuli on the two display, one for each eye. Later, data was down-sampled to time steps of 1/30 s. To make the testing manageable for the subjects each 6.3-minute test was divided into 9 segments of about 42 s duration (Equation 6). Subjects were presented with the segments separated by 7 or more seconds of rest, during which time they could blink freely. Portions of the pupil records with blinks were removed. If more than 15% of a segment was lost due to blinks the segment was repeated. This only occurred in about 1 in 200 segments.

The pupil responses and stimulus histories were then submitted to variants of the response estimation method described above to estimate $F_n = F_n(X, \theta)$. This included simultaneous estimation of the average per-region pupil responses (like those of FIG. 3), i.e. the basis-functions $\varphi_i^r$, and the gain-kernels $h_j^g$. The variations to the method used different numbers and types of symbolic stimulus groups like those in FIGS. 5 and 6, and different numbers of lag-coefficients in the gain-kernels. The objective was to find particular groups and numbers of lag-coefficients that minimized the total number of coefficients in the model ($M_g$ in Equation 2), while at the same time characterizing the pupil responses to the 88-region multifocal stimuli well.

Several methods were used to assess how efficient the different response estimation models were. A simple measure was the proportion of variance in the pupil responses accounted for by the models or $R^2$. Other measures examined the reproducibility of response parameters like the peak amplitude, $A^r$, and the time-to-peak, $t_p^r$. Since control subjects with normal vision and persons with glaucoma were available, the diagnostic power of the pupil response parameters was also examined. The diagnostic power was characterized as the percentage area under the curve (% AUC) for Receiver Operator Characteristic (ROC) plots of the sensitivity on the false positive rate. The achieved gain-kernel coefficients was also fitted using linear mixed effects models. This allowed the average gain-kernel coefficients across subjects, and their SE, to be determined while controlling for multiple comparisons (multiple gain-kernel coefficients within subject). This was performed separately for the control and glaucoma subjects' data. The $R^2$ in these models served as a measure of how consistent the gain-kernel coefficients were across subject groups. By comparing these measures, the optimal number and type of symbolic stimulus groups, and number of gain-kernel lag-coefficients to model pupil responses was determined. The mean gain-kernel lag-coefficients was also examined to obtain some insight into why certain symbolic groups outperformed others. How the coefficients varied across different ages and sexes was also examined.

Table 1 shows the result of fitting an additive linear mixed-effects model to the gain-kernel lag-coefficients obtained from response estimation, where there were 4 symbolic stimulus groups defined as in FIG. 6 COLUMN 4, and the gain-kernels for each group had 3 lag-coefficients, indicating the gain weight for each 0.25 s inter-stimulus interval. Thus the response estimation model contained 12 gain-kernel lag-coefficients. The stimulus was P129 and the subjects were the 94 normal control subjects. Since there were 2 pupils and 2 repeats the data set contained 94×2× 2=376 sets of 12 gain-kernel lag-coefficients. The linear mixed effects model contained a factor for each of the 12 kernel lag-coefficients, and 12 factors for lag by female. Effects for age were also fitted but these were not significant and so are not shown. Table 1 summarizes the results. The model F-statistic was 179 and the adjusted $R^2$ value was 0.698.

The intercept, 0.350, is the average kernel lag-coefficient across the 12 per pupil record for males. Because this is an additive model the next 11 rows: Gain-kernel Coef 2 to Gain-kernel Coef 12, indicate the differences from the Intercept and the significance of those differences. Many of the p-values are very small and are shown as 0.000. Of those labelled p=0.000 the least significant value is $p<8\times10^{-10}$. For those rows the relative significance of the differences is best understood by examining the t-statistic (t-Stat column). The effects for female were less significant but could not be ruled out. The basic message is that the high model $R^2$ of 0.698 means that across the 376 data sets the gain-kernel coefficients were very consistent for this 4-group, 3 lag model gain-kernel model.

Table 2 shows the $R^2$ values for other symbolic group/lag-coefficient response estimation models computed for the 94 normal control subjects. Here data for P129 to P131 were included, so there were 376 sets of gain-coefficients for each of P129 to P131. In fact, the data here differ in one way from those that produced Table 1. Here the pairs of repeat data for each pupil were submitted to a sampling with replacement bootstrap process. In that process 64 synthetic data sets were created from each pair by random sampling with replacement of the 9 segments of each data set. Responses were estimated for these 64 data sets. The idea of these bootstrap cross-validation methods in statistics is to obtain outcomes that more closely reflect the population average. Thus, responses were estimated for 376×64=24,064 data sets for each of P129 to P131. Following this the median values across the 64 for each of the synthetic data sets was taken, and those more robust cross-validated data were submitted to linear mixed effects models as for Table 1.

TABLE 1

| Factor Name | Estimate | SE | t-Stat | p-Value |
| --- | --- | --- | --- | --- |
| (Intercept) | 0.350 | 0.031 | 11.5 | 0.000 |
| Gain-kernel Coef 2 | −0.187 | 0.013 | −14.0 | 0.000 |
| Gain-kernel Coef 3 | −0.387 | 0.013 | −29.8 | 0.000 |
| Gain-kernel Coef 4 | 0.104 | 0.016 | 6.4 | 0.000 |

TABLE 1-continued

| Factor Name | Estimate | SE | t-Stat | p-Value |
| --- | --- | --- | --- | --- |
| Gain-kernel Coef 5 | −0.188 | 0.017 | −11.2 | 0.000 |
| Gain-kernel Coef 6 | −0.302 | 0.016 | −18.8 | 0.000 |
| Gain-kernel Coef 7 | −0.024 | 0.014 | −1.7 | 0.094 |
| Gain-kernel Coef 8 | −0.120 | 0.015 | −8.2 | 0.000 |
| Gain-kernel Coef 9 | −0.391 | 0.014 | −28.1 | 0.000 |
| Gain-kernel Coef 10 | 0.049 | 0.015 | 3.2 | 0.001 |
| Gain-kernel Coef 11 | −0.134 | 0.015 | −8.7 | 0.000 |
| Gain-kernel Coef 12 | −0.306 | 0.015 | −19.9 | 0.000 |
| Gain-kernel Coef Female 1 | −0.006 | 0.018 | −0.3 | 0.755 |
| Gain-kernel Coef Female 2 | 0.032 | 0.018 | 1.8 | 0.077 |
| Gain-kernel Coef Female 3 | −0.004 | 0.017 | −0.2 | 0.830 |
| Gain-kernel Coef Female 4 | 0.027 | 0.023 | 1.2 | 0.241 |
| Gain-kernel Coef Female 5 | 0.028 | 0.023 | 1.2 | 0.220 |
| Gain-kernel Coef Female 6 | 0.014 | 0.022 | 0.6 | 0.522 |
| Gain-kernel Coef Female 7 | 0.094 | 0.019 | 5.0 | 0.000 |
| Gain-kernel Coef Female 8 | −0.049 | 0.019 | −2.6 | 0.011 |
| Gain-kernel Coef Female 9 | 0.041 | 0.018 | 2.3 | 0.024 |
| Gain-kernel Coef Female 10 | 0.047 | 0.021 | 2.3 | 0.023 |
| Gain-kernel Coef Female 11 | −0.013 | 0.021 | −0.6 | 0.521 |
| Gain-kernel Coef Female 12 | 0.002 | 0.021 | 0.1 | 0.926 |

Table 2 shows which response estimation methods produced larger $R^2$ values. As mentioned, larger $R^2$ values mean that the linear models of the average gain-kernel coefficients, like those of Table 1, account for a high proportion of the variance, thus the variation in coefficients is small across the population when $R^2$ is high. The Group 1, 2 and 4 methods respectively used the symbolic stimulus groups of FIG. 5—COLUMN 1 (1 Group, Common Gains), and FIG. 6 COLUMN 4 (4 Groups, By Hemifields), and COLUMN 6 (2 Groups, Switch Eyes). Surprisingly the Switch Eyes symbolic stimulus group, combined with 3 lags, the Groups 2, Lags 3 model of row 4 of Table 2 with its 6 gain-kernel coefficients, gave almost as good consistency (0.740 for P129) as the complex Groups 4, Lags 4 model with its 16 gain-kernel lag-coefficients (0.757 for P129).

TABLE 2

| Response Estimation Model | N Gain-kernel Coefficients | P129 | P130 | P131 |
| --- | --- | --- | --- | --- |
| Groups 1, Lags 1 | 1 | 0.158 | 0.088 | 0.175 |
| Groups 1, Lags 2 | 2 | 0.467 | 0.268 | 0.462 |
| Groups 2, Lags 2 | 4 | 0.438 | 0.248 | 0.427 |
| Groups 2, Lags 3 | 6 | 0.740 | 0.628 | 0.706 |
| Groups 4, Lags 2 | 8 | 0.388 | 0.221 | 0.378 |
| Groups 4, Lags 3 | 12 | 0.691 | 0.557 | 0.641 |
| Groups 4, Lags 4 | 16 | 0.757 | 0.67 | 0.707 |

Table 3 compares different group/lag response estimation methods in terms of diagnostic power and reproducibility metrics. The data are for normal control and glaucoma subjects for P129. Very high ROC values were not expected because the patient's glaucoma was generally mild and 18 of the patient eyes were putatively normal by any diagnostic criteria. Thus, the % ROC values for Sensitivity and Delay are intended to give a relative measure of diagnostic power. In turn diagnostic power is a proxy for delineated true differences in visual fields, whether the intent is for diagnostic purposes or otherwise. Here the $R^2$ values are for the average variance accounted for by the response estimation models and like % ROC, larger means better performance. Srep and Drep are measures of relative repeatability between the pairs of repeats, and for these, smaller numbers mean better performance. Except where indicated, the response estimation models all had 3 lag-coefficients per group in their gain-kernels. The symbolic stimulus group type is indicated by the Group Figure column. These refer to the COLUMNs in FIGS. 5 and 6, thus COL2 means COLUMN 2 of FIG. 5, and COL5 means COLUMN 5 of FIG. 6, and so on. As in Table 2, the best performing model in terms of lowest complexity is for the 2-Group, Switch Eyes symbolic stimulus group assignment. It was much better than the 2-Group, Within Eye method, which had the same number of gain-kernel coefficients.

TABLE 3

| Response Estimation Model | N Gain-kernel Coef | Group Figure | Sensitivity % ROC | Delay % ROC | $R^2$ | Srep | Drep |
|---|---|---|---|---|---|---|---|
| Groups 2, Within Eye | 6 | COL5 | 88.9 | 87.6 | 51.2 | 43.5 | 7.7 |
| Groups 4, By Hemifield | 12 | COL4 | 88.8 | 91.5 | 51.7 | 40.3 | 8.0 |
| Groups 2, Switch Eyes | 6 | COL6 | 89.3 | 92.2 | 51.5 | 40.3 | 8.0 |
| Groups 8, By Hemifield Type | 24 | COL2 | 88.8 | 90.8 | 51.9 | 40.4 | 8.0 |
| Set Gain - Groups 2, Lags 2 | 4 | COL6 | 88.9 | 80.4 | 45.3 | 40.6 | 8.2 |
| Set Gain - Groups 2, Lags 3 | 6 | COL6 | 89.0 | 84.6 | 45.2 | 40.7 | 8.2 |

The bottom two rows of Table 3 that are labelled Set Gain are another type of response estimation model. Here the cross-validated fits for two promising cases were taken from Table 2, fitted mixed effects models as in Table 1, and then forced all the data of the subjects to be fitted to the mean gain-kernels for those two cases when the response estimation was performed. Performance was worse than allowing each pupil to find its best-fitting model. The Set Gain methods demonstrate another non-limiting variation of the basic demonstration. This illustrates that using response estimation models that are tailored to the dynamic gain properties of each individual pupil are superior to the conventional practice of using standard functional expansions like Wiener Kernels.

TABLE 4

A)

| | Group 1 | Group 2 | Group 3 | Group 4 | Group 5 | Group 6 | Group 7 | Group 8 |
|---|---|---|---|---|---|---|---|---|
| Lag 0 | 0.434 | 0.487 | 0.404 | 0.416 | 0.397 | 0.471 | 0.408 | 0.402 |
| Lag 1 | 0.213 | 0.194 | 0.233 | 0.251 | 0.217 | 0.258 | 0.244 | 0.258 |

B) | C)

| | Group 1 | Group 2 | Group 3 | Group 4 | Group 1 | Group 2 | Group 3 | Group 4 |
|---|---|---|---|---|---|---|---|---|
| Lag 0 | 0.413 | 0.487 | 0.395 | 0.419 | 0.321 | 0.418 | 0.327 | 0.378 |
| Lag 1 | 0.228 | 0.226 | 0.253 | 0.252 | 0.196 | 0.206 | 0.227 | 0.209 |
| Lag 2 | −0.037 | 0.071 | −0.035 | 0.070 | 0.005 | 0.080 | 0.009 | 0.075 |

D) | E) | F)

| | Group 1 | Group 2 | Group 1 | Group 2 | Eye 1 | Eye 2 |
|---|---|---|---|---|---|---|
| Lag 0 | 0.324 | 0.396 | 0.323 | 0.386 | 0.351 | 0.346 |
| Lag 1 | 0.209 | 0.208 | 0.187 | 0.197 | 0.184 | 0.199 |
| Lag 2 | 0.006 | 0.077 | | | | |

The question arises, what is it about the two-Group, Switch Eye set of symbolic stimulus groups that makes it efficient? The values of the gain-kernel lag-coefficients for a few cases were investigated. Here models like Table 1 were fitted and the mean values of the coefficients of the gain-kernels that are predicted for persons aged 50 years were examined. Table 4A are the 8 gain-kernels for the 8 Group assignment of FIG. 5, COLUMN 2, fitted with two lags. Lag 0 is the instantaneous gain, Lag 1 the influence upon gain of one 0.25 s step back in time. There is a clear pattern for Lag 0: Groups 2 and 6 have the largest gains. Tables 4B, 4C are for the FIG. 6, COLUMN 4 assignment of groups, where 4B is data from females and 4C from males. They are 3-lag fits. By inspection of COLUMN 2 and COLUMN 4 it is clear that they are similar, but in COLUMN 4 the similar hemifield families are equated by whether they are 3-ring or 2-ring families. As might be expected Group 2 has the largest Lag 0 gain, which correspond to Groups 2 and 6 in Table 4A. Males have slightly smaller gains but the pattern is similar for Lag 0, and the Lag 2 patterns are also similar.

Table 4D is the best performing 2-Group: the Switch Eyes symbolic stimulus group assignment, i.e. FIG. 6 COLUMN 6, with 3 lag coefficients fitted. It has the interesting property of hemifield families of the same side of the eye being pooled, meaning that each step of Group 1 involves a jump to the other eye after a lag of one 0.25 s time step, the same is true for Group 2 and this remains true over all the cycles of the stimuli. Hence, this assignment was called: Switch Eyes. Fitting gain-kernels for these symbolic groups preserves the large lag 0 gain for Group 2 seen for the previous more complex models. Table 4E shows a 2-lag version of the Switch Eyes groups, the results for Lag 0 are similar to Table 4D. FIG. 4F is an example of using the symbolic group assignment of FIG. 6, COLUMN 5; the so-called Within Eyes assignment. Here Group 1 is all the families shown to the left eye and Group 2 those shown to the right eye. The pattern of lag 0 gain being high for group 2 seen in Tables 4A to 4E appears to be lost. Results comparing the 3-lag versions of Switch Eye and Within Eye in Table 3 show that Switch Eyes surprisingly performs better than Within Eyes although they have the same number of groups and gain-kernel lag-coefficients.

The fact that Switch Eyes works so well indicates that there must be an eye dependent component of gain. This was not anticipated because previous work reported in U.S. Pat. No. 9,848,771 indicated that gain changes occurred in the Edinger-Westphal Nucleus where input from the two eyes is brought together and summed, seemingly removing the possibility of eye-dependent gain change. The Switch Eyes assignment groups together stimuli from eyes that have not seen a stimulus for close to 0.5 s capturing their resulting higher dynamic gain state. Taken together this evidence suggests an unsuspected strong regulation of responsiveness at the level of the Pretectal Olivary Nucleus or lower down in the path from the retina to the pupils.

According to one example, where there may be more than one type of hemifield or quadrant complementary set, for example if the multifocal array consisted of 5 rings of stimuli centered on fixation and half the hemifield or quadrants were drawn from either rings 1, 3, 5 or from rings 2, 4, making for two types of hemifield or quadrant volleys, so that a cycle of the many round-robin cycles of volleys would have 8 type of volleys, but again only two symbolic stimulus groups and two gain-kernels may be measured to capture a switch eyes pattern of symbolic stimulus group assignments.

Overall, the aims of the experiments have been met. Estimating gain-kernels and per-region temporal impulse response together improves the value of the responses estimated. Particular parsimonious assignments of symbolic stimulus groups allow response estimation models to be fitted that are as efficient and consistent as estimation models with 2 to 4 times more gain-kernel lag-coefficients. These discoveries were quite unexpected and not anticipated by any prior art. The inclusion of gain-kernels into response estimation models in order to capture dynamic change in gain is also advantageous.

Demonstration 2

In the first demonstration basis-functions were used that were parametrically defined log-normal functions (Eq. 5). It is mentioned herein of the possibility of using bilinear basis-functions, rather than parametric basis-functions. It is therefore shown that the advantage of estimating gain-kernels also occurs when alternative basis-functions are estimated. For this demonstration data from 170 normal control subjects was used. These persons were tested with the previously described 44-region per eye P129 and P130 multifocal stimuli, with both eyes being tested concurrently and both pupils recorded with apparatus as in FIG. 2. Each subject was tested twice about 2 weeks apart. Response estimates were obtained without including gain-kernels and with gain-kernels for the 4 Groups by hemifield assignment of symbolic stimulus groups of FIG. 6 COLUMN 4. The resulting fitted gain coefficients are thus similar to those of Tables 4B, 4C.

Figure 9:
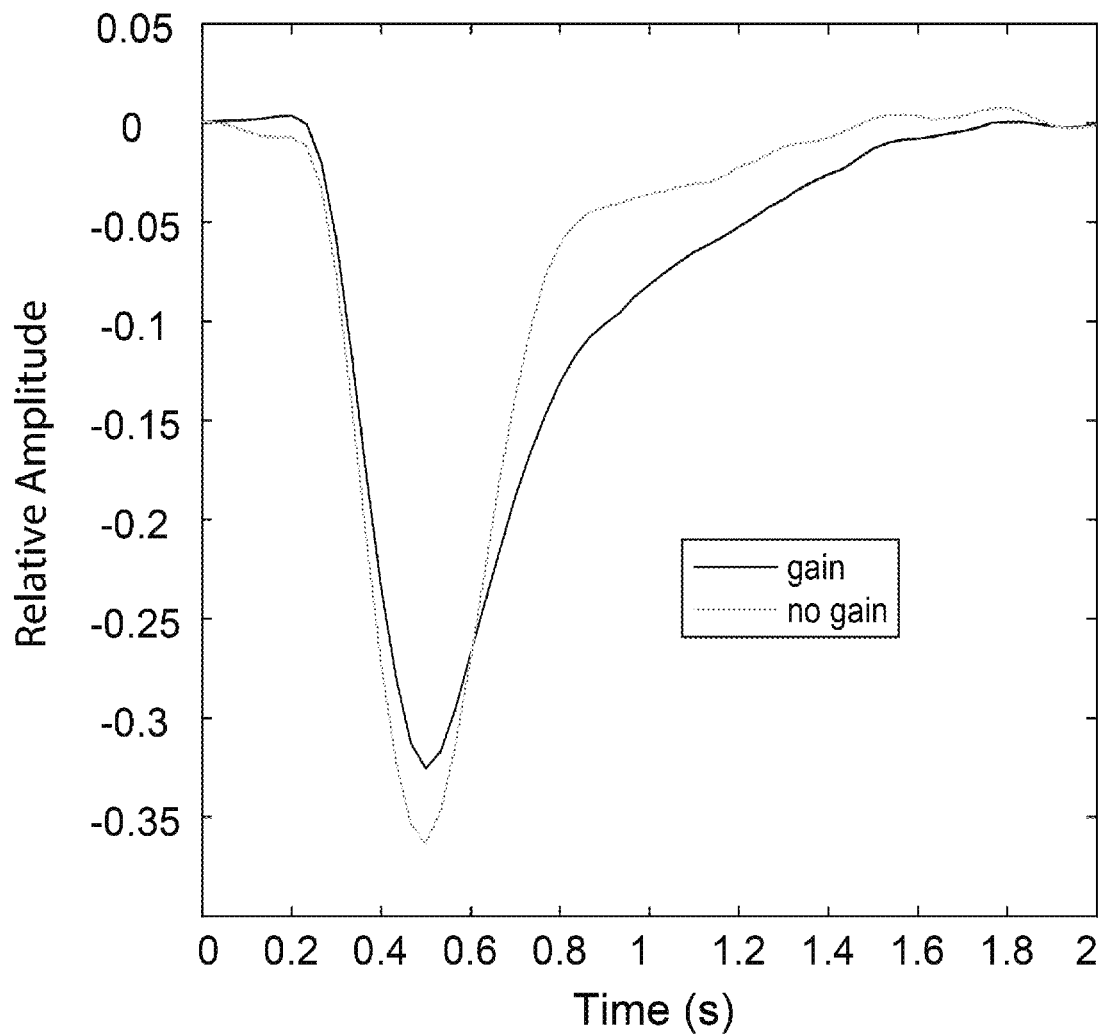
FIG. 9 Shows the difference in bilinear basis-function waveforms obtained when gain-kernels are included in the response estimates (black waveform, gain); or are not included (grey waveform, no gain). These are the median basis-functions computed across pupils, repeats and 170 normal subjects tested with a P129 stimulus array.

FIG. 9 shows the result of averaging the estimated bilinear basis-functions, across pupils, subjects and repeats, demonstrating the effect of including gain-kernels in the response estimation for the P129 stimulus protocol. The waveforms are thus means of 170 subjects×2 pupils×2 repeats=680 estimated bilinear basis-functions. The legend indicates that the black curve (gain in the legend) is the average basis-function for the case of estimating the gain-kernels as described above. The grey curve (no gain in the legend) is the outcome when no gain-kernels are fitted. The basis-function waveforms are noticeably different. The basis-function obtained with the gain-kernels estimated peaks later and recovers to baseline pupil size (0 on the vertical scale) more slowly. Thus, fitting gain-kernels alters the timing of the estimated responses.

Along with estimating a basis-function for each pupil the response estimation process of equations 9 and 10 also estimates 44 coefficients, i.e. weights, to be applied to each basis-function to create the estimated response waveforms for each region. For a given pupil there is a 61×1 vector bf containing the basis-function waveform. There is also a 44×1 vector cf containing values that are coefficients, i.e. weights, to be applied to each basis-function for each of the 44 P129 test regions per eye. Then the matrix-multiplication: $wf=bf \times cf^T$, where T is the transpose, creates the 61×44 matrix, wf, of estimated response waveforms for a single basis function. Given this outer product of vectors the process can be referred to as bilinear. In fact, bf and cf are estimated simultaneously for the 88 regions covered by each pupil record.

Table 5 summarizes differences in the outcomes of the two types of response estimation methods: with (Gain) and without gain-kernel (no Gain) estimation. All table entries are the medians across the 680 estimates. Given the large numbers, any differences in the means are highly significantly different even when multiple comparisons are accounted for. The amplitude of the peak pupil constrictions are much larger for the gain-kernel case (second row, labelled Gain), than for the case of not fitting gain-kernels (row 1, labelled No Gain). This was true for both P129 and 130. The t-statistics, that is the per-region constriction amplitudes divided by their per-region SE, provide a measure of per-region signal to noise ratios, and are much larger for the gain-kernel versions. Similarly, the mean $R^2$ values for the gain-kernel inclusive models are larger. As mentioned for FIG. 9 the times-to-peak are longer. Overall the addition of gain-kernels to the response estimation process improves the goodness of fit and signal to noise ratio when a single bilinear basis-function per pupil is used.

TABLE 5

| | Amplitude (μm) | | t-statistic | | $R^2$ | | Time-to-peak (ms) | |
| --- | --- | --- | --- | --- | --- | --- | --- | --- |
| Stimulus | P129 | P130 | P129 | P130 | P129 | P130 | P129 | P130 |
| No Gain | 15.3 | 13.8 | 3.55 | 3.29 | 0.482 | 0.421 | 501.7 | 509.1 |
| Gain | 21.1 | 17.5 | 4.28 | 3.64 | 0.498 | 0.435 | 511.3 | 522.8 |

Demonstration 3

As indicated by Eq. 10 and associated text it is also possible to have two or more (1) bilinear basis-functions per pupil, where during the iterative fit, singular value decomposition is used to estimate an orthonormal set of 4p basis-functions for j=1, . . . , 1. For the present demonstration with 2 orthonormal basis-functions per pupil the gain-kernels were estimated for the 4 Groups using the Hemi-fields assignment of symbolic stimulus groups from FIG. 6 COLUMN 4, as in the previous demonstration. The resulting fitted gain coefficients are thus similar in form to those of Tables 4B, 4C, and like those, this preserves the large Lag 0 gain for Group 2 seen for Switch Eyes assignment of symbolic groups.

Figure 10:
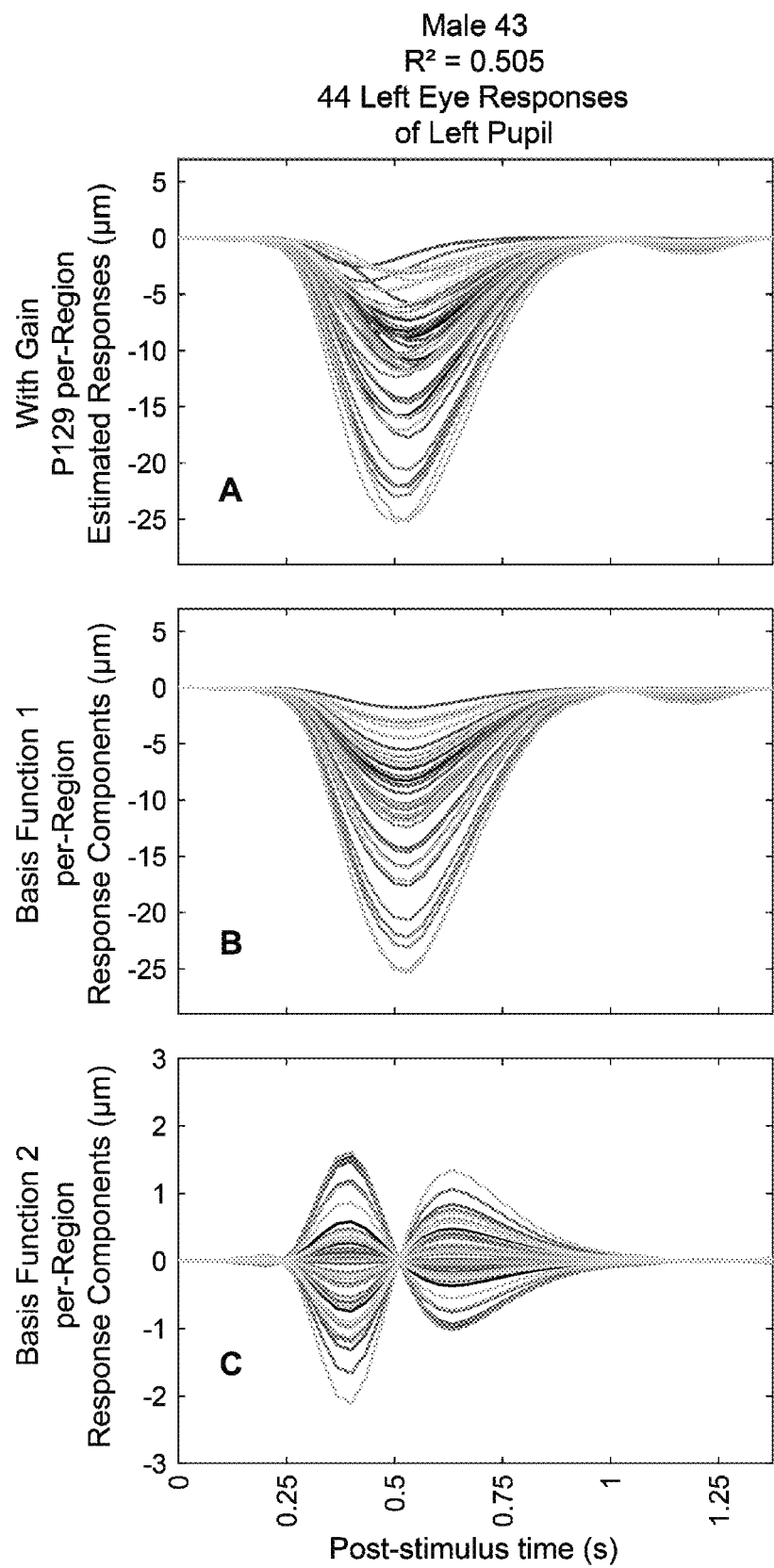
FIG. 10 Shows an example of the responses estimated for two orthonormal basis-functions per pupil, referred to here as basis-functions 1 and 2. The waveforms are estimates of the responses of the left pupil to stimulation of the left eye of a 43-year-old male subject using the P129 stimulus array.
Figure 11:
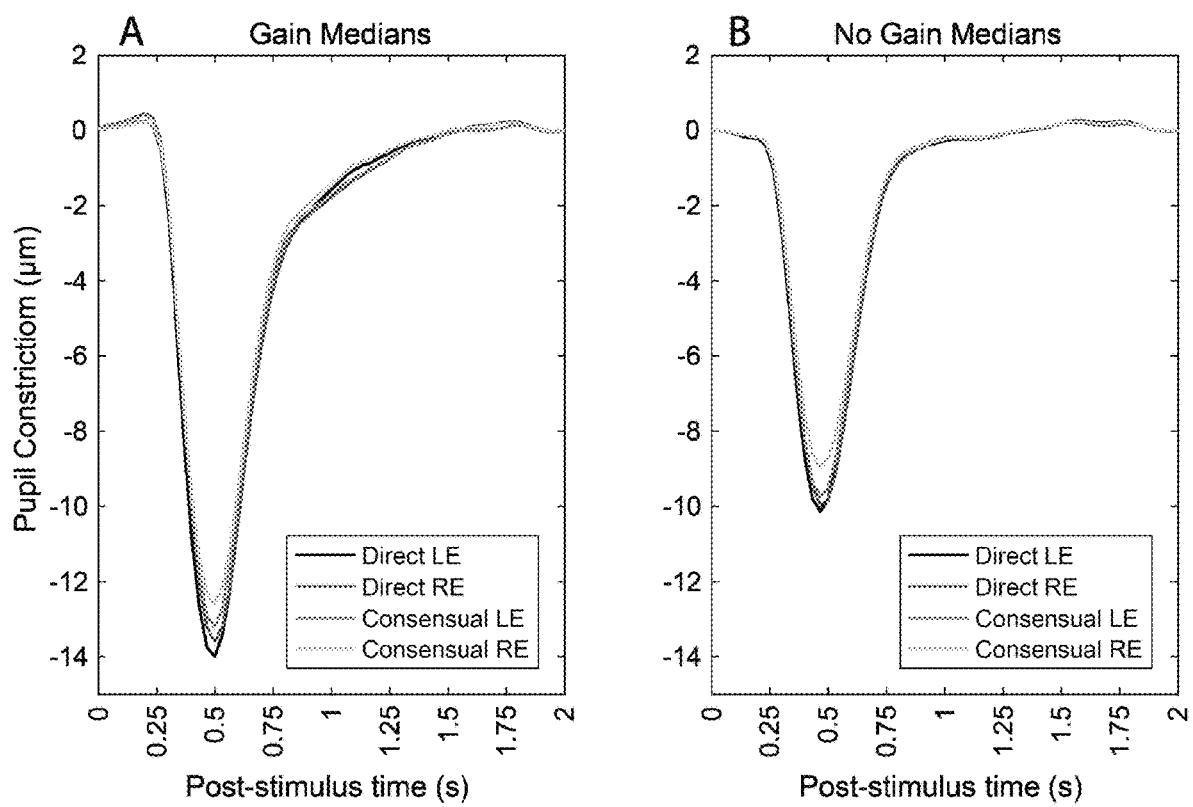
FIG. 11 Illustrates the median response waveforms computed across the 44 stimulus regions, and 170 subjects for the left and right eyes (LE and RE) as recorded by the left and right pupils. When a pupil reports on stimulation of its own eye that is called a Direct response. Conversely, when a pupil reports on stimulation of its fellow eye that is called a Consensual response. The legend indicates which grey level corresponds to the Direct and Consensual responses for the two eyes (LE and RE). Each of the averaged waveforms was created by the two component bilinear method of FIG. 10 and Equation 10.

FIG. 10 illustrates the use of two orthonormal basis-functions for estimating responses of a single pupil. In this example the pupil is the left pupil and the illustrated responses in FIG. 10A are those arising by stimulation of the left eye of a 43-year-old male employing the 44-region P129 stimulus described above. The 44 estimated responses are shown as 44 waveforms having different grey levels in FIG. 10A. It is worth noting that the 44 estimated per-region waveforms have different peak constriction amplitudes and times-to-peak. These are achieved by summing different ad-mixtures of the two basis-functions found by the iterative fitting process, as suggested by the text above associated with Equation 10.

As for a single bilinear basis-function matrix-multiplication is used to construction the 44 responses of FIG. 10A from two basis-functions. Consider the 61×2 matrix bf where the values of columns describe the 1=2 basis-function waveforms. Next consider the 44×2 matrix cf containing values that are coefficients, i.e. weights, to be applied to each basis-function for each of the 44 P129 test regions per eye. Then the matrix-multiplication $wf=bf \times cf^T$, where T is the transpose, creates the 61×44 matrix wf of estimated response waveforms. Alternatively, one can make the computation in two steps for each basis-function for each column $bf_1$ and $cf_1$: $wf_1=bf_1 \times cf_1^T$, and $wf_2=bf_2 \times cf_2^T$, and so $wf=wf_1+wf_2$. In this case $wf_1$ and $wf_2$ can be thought of as two sets of per-region response component waveforms based upon their respective basis-functions. FIG. 10 illustrates that process for one pupil of one eye of a subject, where the waveforms of FIG. 10A are the sums of waveforms in FIGS. 10B and 10C.

TABLE 6

|  | Amplitude (μm) | Amplitude t-statistic | $R^2 \pm SD$ | Component 1 t-statistic | Component 2 t-statistic |
|---|---|---|---|---|---|
| No Gain | 10.4 | 2.39 | 0.393 ± 0.151 | 2.19 | 0.592 |
| Gain | 14.0 | 3.36 | 0.496 ± 0.135 | 3.17 | 0.655 |
| Ratio | 1.35 | 1.41 | 1.26 | 1.45 | 1.11 |

Table 6 shows the results of including or not including gain-kernels in the estimation of the two bilinear basis-function method. The top row, labelled No Gain at left, are data obtained without including gain-kernel estimates, and the second row labelled Gain are for the case of including gain-kernels in the response estimates. The bottom row are the ratios of the Gain/No Gain cases. As in Demonstration 2, the data are pooled across the two eyes and pupils of the 170 normal subjects who took the P129 test twice. The first column is the median peak per-region response constriction amplitude, and the second the t-statistics for those amplitudes. Next are the $R^2$ goodness of fit statistics±their standard deviations (SD). The t-statistics for the per-region weights (cf above) are also given, response components 1 and 2 referring to those generated from basis-functions 1 and 2. In all cases, including the gain-kernels improves all aspects of the fitted values. The two basis-function fits provide flexibility in terms of times-to-peak and waveform shape. Flexibility of waveform shape could be useful if the stimuli had longer, non-impulsive time courses.

The data for Component 2 of Table 6 does indicate a possible short-coming of the bilinear basis function method: the t-statistics for Component 2 are small. In fact, the absolute values of the t-statistics were taken before averaging because they can be of either sign (e.g. FIG. 10C). Nevertheless, they are <2 indicating that they are non-significantly different than 0 on average. This might suggest gaining flexibility by using a parametric basis function, like the log-normal function of Equation 5, but also including its temporal derivative in the response estimation process for the addition of one extra parameter per region.

Demonstration 4

Up to this point it has been assumed that the positive and negative going values of the contrast sequence, $c_n^g$ of equation 1 and its sum $c_n$, should be treated the same when it comes to estimating gain-kernels. As shown by Equation 11 and associated text, those stimulus data can be split into positive (ON) and negative (OFF) contrasts and separate gain-kernels can be estimated for each, allowing a broader class of response models to be estimated. In particular, the models could encompass the possibly of the pupil system having different gains for positive and negative going contrast sequences. Here single log-normal parametric basis-functions per test region are used, each having its own per-region estimated peak value, i.e. amplitude, and time-to-peak.

Table 7 shows the resulting fitted gain-kernel coefficients for the ON and OFF contrasts for the 4 Groups by Hemifields assignment of symbolic stimulus groups of FIG. 6 COLUMN 4. As before, 3 lags are included. Table 7 thus follows the format for Tables 4B, 4C but with separate entries for the simultaneously estimated ON and OFF gain coefficients. Like Tables 4B, 4C the largest gain was for Group 2 Lag 0. When investigated, the OFF gains were actually larger than the ON, especially for Lag 0, Group 2, an unanticipated and advantageous outcome. The t-statistics for the coefficients in the left columns labelled Group 1 to Group 4, are given in the similarly labelled right-most four columns. The Lag 1 t-statistics for the OFF gain coefficients were surprisingly significant compared to those for ON gain. This was also unexpected and revealed more about the pupillary system.

TABLE 7

| | Gain-kernel Coefficients | | | | t-statistics | | | |
|---|---|---|---|---|---|---|---|---|
| | Group 1 | Group 2 | Group 3 | Group 4 | Group 1 | Group 2 | Group 3 | Group 4 |
| | A - ON Gain | | | | | | | |
| Lag 0 | 0.31 | 0.36 | 0.29 | 0.34 | 5.79 | 4.76 | 4.82 | 4.61 |
| Lag 1 | 0.13 | 0.05 | 0.14 | 0.06 | 1.72 | 0.49 | 1.64 | 0.55 |
| Lag 2 | −0.03 | 0.03 | −0.04 | 0.02 | −0.48 | 0.31 | −0.47 | 0.16 |
| | B - OFF Gain | | | | | | | |
| Lag 0 | 0.48 | 0.73 | 0.43 | 0.50 | 3.78 | 4.16 | 3.08 | 3.06 |
| Lag 1 | 0.28 | 0.40 | 0.34 | 0.40 | 3.57 | 3.48 | 3.74 | 3.61 |
| Lag 2 | −0.01 | 0.11 | 0.01 | 0.11 | −0.12 | 1.10 | 0.17 | 1.13 |

The invention claimed is:

1. A method for assessing the visual nervous system of a subject, the method comprising the steps of:
presenting, via a plurality of light sources controlled by at least one computer, in a statistically independent sequence of time steps, multifocal ensembles of stimuli within portions of a visual field or fields of an eye or eyes of the subject, each multifocal ensemble of stimuli adapted to evoke pupillary responses from at least one pupil of the subject, each multifocal ensemble of stimuli comprising a plurality of individual stimulus elements concurrently presented to different component parts of the visual field or fields;
detecting, using at least one sensor, pupillary responses to the presented multifocal ensembles of stimuli;
the at least one computer measuring dynamic changes in pupil response gain based on the detected pupillary responses, wherein the measuring includes representing stimulus elements presented to different component parts of the visual field or fields by a smaller number of symbolic groups of stimulus regions, wherein each symbolic group of stimulus regions is formed from a unique subset of the component parts of the visual field or fields, and measuring a dynamic change in pupil response gain for each symbolic group of stimulus regions based on the detected pupillary responses to stimulus elements presented to the component parts of the visual field or fields of the symbolic group of stimulus regions; and
the at least one computer measuring temporal impulse responses to each of the plurality of individual stimulus elements based on the measured dynamic change in pupil response gain for the symbolic group of stimulus regions corresponding to the component part of the visual field stimulated by the individual stimulus element.

2. The method of claim 1, wherein each of the different component parts of the visual field or fields is assigned to one of a plurality of families, and where, on any time step, the plurality of individual stimulus elements of the multifocal ensemble of stimuli are selected from one of the plurality of families and presented, and wherein each family is in turn assigned to the same or a smaller number of the symbolic groups of stimulus regions, and wherein the dynamic changes in pupil response gain are only measured for the individual stimulus elements defined by the same or smaller number of symbolic groups of stimulus regions by measuring at least one gain-kernel for each symbolic group of stimulus regions.

3. The method of claim 2, wherein the visual field of each eye is divided into two complementary quadrant pairs, wherein each quadrant pair is one of: a hemifield or diagonally opposed quadrants, and in which, on particular time steps, multifocal ensembles of stimuli are presented to the visual fields of two eyes in cycling volleys, where the volleys of multifocal ensembles of stimuli comprise individual stimulus elements chosen at random from the component parts of the visual field belonging to one of the two complementary quadrant pairs of the visual field of one of the two eyes, and on successive time steps the volleys of multifocal ensembles of stimuli are presented to each of the complementary quadrant pairs of a first eye, then each of the complementary quadrant pairs of a second eye, and where the probability of an individual stimulus element from any of the complementary quadrant pairs of the first and second eyes being presented on a corresponding time step is about 50%, and a sequence of the volleys repeats cyclically a plurality of times, and the stimulus elements for the complementary quadrant pairs of the first and second eyes are assigned to symbolic groups of stimulus regions.

4. The method of claim 3, wherein the complementary quadrant pairs are left and right hemifields, wherein the stimulus elements presented to the left hemifield of the first and second eyes are assigned to a first symbolic group of stimulus regions, and the stimulus elements presented to the right hemifield of the first and second eyes are assigned to a second symbolic group of stimulus regions, and the dynamic changes in pupil response gain are measured only for the first and second symbolic groups of stimulus regions, and the impulse responses are measured for every stimulus element based on the measured dynamic changes in pupil response gain.

5. The method of claim 3, wherein the complementary quadrant pairs are left and right hemifields, wherein the stimulus elements presented to the left hemifield of the first eye are assigned to a first symbolic group of stimulus regions, the stimulus elements presented to the right hemifield of the first eye are assigned to a second symbolic group of stimulus regions, the stimulus elements presented to the left hemifield of the second eye are assigned to a third symbolic group of stimulus regions, the stimulus elements presented to the right hemifield of the second eye are assigned to a fourth symbolic group of stimulus regions, and the dynamic changes in pupil response gain are measured only for the first, second, third and fourth symbolic groups of stimulus regions, and the impulse responses are measured for every stimulus element based on the measured dynamic changes in pupil response gain.

6. The method of claim 3, wherein the complementary quadrant pairs are upper and lower hemifields, wherein the stimulus elements presented to an upper hemifield of the first eye are assigned to a first symbolic group of stimulus regions, the stimulus elements presented to a lower hemifield of the first eye are assigned to a second symbolic group of stimulus regions, the stimulus elements presented to an upper hemifield of the second eye are assigned to a third symbolic group of stimulus regions, the stimulus elements presented to a lower hemifield of the second eye are assigned to a fourth symbolic group of stimulus regions, and the dynamic changes in pupil response gain are measured only for the first, second, third and fourth symbolic groups of stimulus regions, and the impulse responses are measured for every stimulus element based on the measured dynamic changes in pupil response gain.

7. The method of claim 3, wherein the complementary quadrant pairs are diagonally opposed quadrants, wherein the symbolic groups of stimulus regions are arranged based on a first complementary quadrant pair of the visual field for both the first and second eyes and a second complementary quadrant pair of the visual field for both the first and second eyes, and the dynamic changes in pupil response gain are measured only for the symbolic groups of stimulus regions, and the impulse responses are measured for every stimulus element based on the measured dynamic changes in pupil response gain.

8. The method of claim 3, wherein the smaller number of symbolic groups of stimulus regions includes two symbolic groups of stimulus regions, and wherein two dynamic changes in pupil response gain are measured to capture dynamic changes in pupil response quantifying a switch eyes pattern of symbolic group of stimulus regions assignments.

9. The method of claim 3, wherein for an even number of N types of complementary quadrant pair volleys, the stimulus elements presented to different component parts of the visual field or fields are represented by N/2 symbolic groups of stimulus regions, and a gain-kernel is measured for each symbolic group of stimulus regions to capture a switch eyes pattern of symbolic groups of stimulus regions assignments.

10. The method of claim 2, wherein, for each symbolic group of stimulus regions, the component parts of the visual field or fields are divided into a plurality of levels based on a number of stimulus elements presented to each of the component parts of the visual field or fields, and wherein a single gain-kernel is measured for each of the plurality of levels in the symbolic group of stimulus regions.

11. The method of claim 2, wherein the visual fields of both eyes are stimulated by the presentation of the multifocal ensembles of stimuli comprising four subsets of stimulus elements that stimulate a first complementary part and a second complementary part of the visual fields of the two eyes, wherein the assignment to two symbolic groups of stimulus regions follows the sequence of the first complementary part that is presented to the first eye being assigned to a first group of the symbolic groups of stimulus regions, the second complementary part that is presented to the first eye being assigned to a second group of the symbolic groups of stimulus regions, the first complementary part that is presented to the second eye being assigned to the first group, the second complementary part that is presented to the second eye being assigned to the first group, wherein the presenting includes repeating, in a round-robin fashion, multifocal ensembles of stimuli comprising stimulus elements selected from one of the four subsets of stimulus elements, and wherein the impulse responses are measured for every stimulus element based on the measured dynamic changes in pupil response gain only for the first group and the second group.

12. The method of claim 11, wherein the multifocal ensembles of stimuli comprise sporadic departures from the set pattern of the first complementary part and the second complementary part, wherein a sporadic departure comprises a stimulus element in the multifocal ensemble of stimuli located outside of the corresponding first or second complementary part for the multifocal ensemble of stimuli.

13. The method of claim 1, wherein the temporal impulse responses are measured as a parametric function of a limited number of parameters for each portion of the visual field using a log-normal distribution.

14. The method of claim 13, wherein a temporal derivative of the parametric function is used in the response measurement.

15. The method of claim 1, wherein the temporal impulse responses are measured as a set of one or more bilinear orthonormal basis functions.

16. A computer system for assessing the visual nervous system of a subject, the computer system comprising:
   at least one computer;
   a plurality of light sources controlled by the at least one computer, the plurality of light sources arranged to present under control of the at least one computer, in a statistically independent sequence of time steps, multifocal ensembles of stimuli within portions of a visual field or fields of an eye or eyes of the subject, each multifocal ensemble of stimuli adapted to evoke pupillary responses from at least one pupil of the subject, each multifocal ensemble of stimuli comprising a plurality of individual stimulus elements presented to different component parts of the visual field or fields;
   at least two sensors arranged to detect pupillary responses to the presented multifocal ensembles of stimuli;
   wherein the at least one computer is arranged to:
      measure dynamic changes in pupil response gain based on the detected pupillary responses, wherein the measuring includes representing stimulus elements presented to different component parts of the visual field or fields by a smaller number of symbolic groups of stimulus regions, wherein each symbolic group of stimulus regions is formed from a unique subset of the component parts of the visual field or fields, and measuring a dynamic change in pupil response gain for each symbolic group of stimulus regions based on the detected pupillary responses to stimulus elements presented to the component parts of the visual field or fields of the symbolic group of stimulus regions; and
      measure temporal impulse responses to each of the plurality of individual stimulus elements based on the measured dynamic change in pupil response gain for the symbolic group of stimulus regions corresponding to the component part of the visual field stimulated by the individual stimulus element.

17. The computer system of claim 16, wherein each of the different component parts of the visual field or fields is assigned to one of a plurality of families, and wherein the plurality of light sources are controlled by the at least one computer to, on any time step, present a plurality of individual stimulus elements of the multifocal ensemble of stimuli selected from one of the plurality of families, and wherein each family is in turn assigned to the same or a smaller number of the symbolic groups of stimulus regions, and wherein the at least one computer is arranged to only measure the dynamic changes in pupil response gain for the individual stimulus elements defined by the same or smaller number of symbolic groups of stimulus regions by measuring at least one gain-kernel for each symbolic group of stimulus regions.

18. The computer system of claim 17, wherein the visual field of each eye is divided into two complementary quadrant pairs, wherein each quadrant pair is one of: a hemifield or diagonally opposed quadrants, and wherein the plurality of light sources are controlled by the at least one computer to, on particular time steps, present multifocal ensembles of stimuli to the visual fields of two eyes in cycling volleys, where the volleys of multifocal ensembles of stimuli comprise individual stimulus elements are chosen at random by the at least one computer from the component parts of the visual field belonging to one of the two complementary quadrant pairs of the visual field of one of the two eyes, and on successive time steps the plurality of light sources are controlled by the at least one computer to present volleys of multifocal ensembles of stimuli to each of the complementary quadrant pairs of a first eye, and then to each of the complementary quadrant pairs of a second eye, and where the probability of an individual stimulus element from any of the complementary quadrant pairs of the first and second eyes being presented on a corresponding time step is about 50%, and a sequence of the volleys repeats cyclically a plurality of times, and the stimulus elements for the complementary quadrant pairs of the first and second eyes are assigned to symbolic groups of stimulus regions.

19. The computer system of claim 18, wherein the complementary quadrant pairs are left and right hemifields, wherein the stimulus elements presented to the left hemifield of the first and second eyes are assigned by the at least one computer to a first symbolic group of stimulus regions, and the stimulus elements presented to the right hemifield of the first and second eyes are assigned by the at least one computer to a second symbolic group of stimulus regions, and the at least one computer is arranged to measure dynamic changes in pupil response gain only for the first and second symbolic group of stimulus regions, and further arranged to measure the impulse responses for every stimulus element based on the measured dynamic changes in pupil response gain.

20. The computer system of claim 18, wherein the complementary quadrant pairs are left and right hemifields, wherein the stimulus elements presented to the left hemifield of the first eye are assigned by the at least one computer to a first symbolic group of stimulus regions, the stimulus elements presented to the right hemifield of the first eye are assigned by the at least one computer to a second symbolic group of stimulus regions, the stimulus elements presented to the left hemifield of the second eye are assigned by the at least one computer to a third symbolic group of stimulus regions, the stimulus elements presented to the right hemifield of the second eye are assigned by the at least one computer to a fourth symbolic group of stimulus regions, and the at least one computer is arranged to measure the dynamic changes in pupil response gain only for the first, second, third and fourth symbolic groups of stimulus regions, and further arranged to measure the impulse responses for every stimulus element based on the measured dynamic changes in pupil response gain.

21. The computer system of claim 18, wherein the complementary quadrant pairs are upper and lower hemifields, wherein the stimulus elements presented to an upper hemifield of the first eye are assigned by the at least one computer to a first symbolic group of stimulus regions, the stimulus elements presented to a lower hemifield of the first eye are assigned by the at least one computer to a second symbolic group of stimulus regions, the stimulus elements presented to an upper hemifield of the second eye are assigned by the at least one computer to a third symbolic group of stimulus regions, the stimulus elements presented to a lower hemifield of the second eye are assigned by the at least one computer to a fourth symbolic group of stimulus regions, and the at least one computer is arranged to measure the dynamic changes in pupil response gain only for the first, second, third and fourth symbolic stimulus groups, and further arranged to measure the impulse responses for every stimulus element based on the measured dynamic changes in pupil response gain.

22. The computer system of claim 18, wherein the complementary quadrant pairs are diagonally opposed quadrants, wherein the symbolic groups of stimulus regions are arranged by the at least one computer based on a first complementary quadrant pair of the visual field for both the first and second eyes and a second complementary quadrant pair of the visual field for both the first and second eyes, and the at least one computer is arranged to measure the dynamic changes in pupil response gain only for the symbolic groups of stimulus regions, and the at least one computer is further arranged to measure the impulse responses for every stimulus element based on the measured dynamic changes in pupil response gain.

23. The computer system of claim 18, wherein the smaller number of symbolic groups of stimulus regions includes two symbolic groups of stimulus regions, and wherein two dynamic changes in pupil response gain are measured to capture dynamic changes in pupil response quantifying a switch eyes pattern of symbolic group of stimulus regions assignments.

24. The computer system of claim 18, wherein for an even number of N types of complementary quadrant pair volleys, the stimulus elements presented to different component parts of the visual field or fields are represented by N/2 symbolic groups of stimulus regions, and a gain-kernel is measured for each symbolic group of stimulus regions by the at least one computer to capture a switch eyes pattern of symbolic group of stimulus regions assignments.

25. The computer system of claim 17, wherein, for each symbolic group of stimulus regions, the component parts of the visual field or fields are divided into a plurality of levels based on a number of stimulus elements presented to each of the component parts of the visual field or fields, and wherein a single gain-kernel is measured for each of the plurality of levels in the symbolic group of stimulus regions.

26. The computer system of claim 17, wherein the plurality of light sources are arranged, under control of the at least one computer, to stimulate visual fields of both eyes by presenting the multifocal ensembles of stimuli comprising four subsets of stimulus elements that stimulate a first complementary part and a second complementary part of the visual fields of the two eyes, wherein the assignment to two symbolic groups of stimulus regions follows the sequence of the first complementary part that is presented to the first eye being assigned by the at least one computer to a first group of the symbolic groups of stimulus regions, the second complementary part that is presented to the first eye being assigned by the at least one computer to a second group of the symbolic groups of stimulus regions, the first complementary part that is presented to the second eye being assigned by the at least one computer to the first group, the second complementary part that is presented to the second eye being assigned by the at least one computer to the first group, where the at least one computer is arranged to present multifocal ensembles of stimuli comprising stimulus elements selected from one of the four subsets of stimulus elements in a repeating, round-robin fashion and measure the impulse responses for every stimulus element based on the measured dynamic changes in pupil response gain only for the first group and the second group.

27. The computer system of claim 26, wherein the multifocal ensembles of stimuli comprise sporadic departures from the set pattern of the first complementary part and the second complementary part, wherein a sporadic departure comprises a stimulus element in the multifocal ensemble of stimuli located outside of the corresponding first or second complementary part for the multifocal ensemble of stimuli.

28. The computer system of claim 16, wherein the at least one computer is arranged to measure the temporal impulse responses as a parametric function of a limited number of parameters for each portion of the visual field using a log-normal distribution.

29. The computer system of claim 28, wherein the at least one computer is arranged to use a temporal derivative of the parametric function in the response measurement.

30. The computer system of claim 16, wherein the at least one computer is arranged to measure the temporal impulse responses as a set of one or more bilinear orthonormal basis functions.

* * * * *